(12) United States Patent
Callahan et al.

(10) Patent No.: US 11,957,810 B2
(45) Date of Patent: Apr. 16, 2024

(54) ULTRAVIOLET LIGHT SANITIZING PACING SYSTEMS AND METHODS

(71) Applicant: THE BOEING COMPANY, Chicago, IL (US)

(72) Inventors: Kevin S. Callahan, Shoreline, WA (US); Jamie J. Childress, Mercer Island, WA (US)

(73) Assignee: The Boeing Company, Chicago, IL (US)

( * ) Notice: Subject to any disclaimer, the term of this patent is extended or adjusted under 35 U.S.C. 154(b) by 800 days.

(21) Appl. No.: 17/026,414

(22) Filed: Sep. 21, 2020

(65) Prior Publication Data
US 2021/0346561 A1 Nov. 11, 2021

Related U.S. Application Data

(63) Continuation-in-part of application No. 17/020,942, filed on Sep. 15, 2020, and a continuation-in-part of application No. 29/735,235, filed on May 19, 2020.
(Continued)

(51) Int. Cl.
*A61L 2/28* (2006.01)
*A61L 2/10* (2006.01)

(52) U.S. Cl.
CPC ........ *A61L 2/28* (2013.01); *A61L 2/10* (2013.01); *A61L 2202/11* (2013.01);
(Continued)

(58) Field of Classification Search
CPC .......... A61L 2/28; A61L 2/10; A61L 2202/11; A61L 2202/14; A61L 2202/16; A61L 2202/25
See application file for complete search history.

(56) References Cited

U.S. PATENT DOCUMENTS

| 10,232,954 B2 | 3/2019 | Boeing |
| 10,363,329 B2 | 7/2019 | Boeing |

(Continued)

FOREIGN PATENT DOCUMENTS

| EP | 352238 | 7/2019 |
| EP | 3915592 | 12/2021 |

(Continued)

OTHER PUBLICATIONS

U.S. Appl. No. 17/016,466, filed Sep. 10, 2020.
(Continued)

*Primary Examiner* — Regina M Yoo
(74) *Attorney, Agent, or Firm* — Joseph M. Butscher; The Small Patent Law Group, LLC

(57) ABSTRACT

An ultraviolet (UV) light pacing system includes an assembly including a UV lamp configured to emit UV light to disinfect a component. One or more range light sources are configured to emit ranging light. At least one aspect of the ranging light is altered to provide a visual cue for guiding motion of the assembly to disinfect the component. An ultraviolet (UV) light pacing method includes emitting ranging light from one or more range light sources of and assembly having a UV lamp configured to emit UV light to disinfect a surface of a component, and altering at least one aspect of the ranging light to provide a visual cue for guiding motion of the assembly to disinfect the component.

28 Claims, 27 Drawing Sheets

Related U.S. Application Data

(60) Provisional application No. 63/067,999, filed on Aug. 20, 2020, provisional application No. 63/037,630, filed on Jun. 11, 2020, provisional application No. 63/037,039, filed on Jun. 10, 2020, provisional application No. 63/027,869, filed on May 20, 2020, provisional application No. 63/021,984, filed on May 8, 2020.

(52) U.S. Cl.
 CPC ....... *A61L 2202/14* (2013.01); *A61L 2202/16* (2013.01); *A61L 2202/25* (2013.01)

(56) References Cited

U.S. PATENT DOCUMENTS

| | | | |
|---|---|---|---|
| 11,007,292 B1* | 5/2021 | Grenon | A61L 2/24 |
| 2006/0165571 A1* | 7/2006 | Seon | A61J 11/008 |
| | | | 422/305 |
| 2008/0260601 A1 | 10/2008 | Lyon | |
| 2010/0044582 A1* | 2/2010 | Cooper | A61L 2/10 |
| | | | 250/455.11 |
| 2012/0068088 A1* | 3/2012 | Durkin | A61L 2/10 |
| | | | 250/492.1 |
| 2012/0219699 A1* | 8/2012 | Pettersson | B05B 12/124 |
| | | | 427/8 |
| 2015/0359915 A1 | 12/2015 | Farren | |
| 2016/0101202 A1* | 4/2016 | Gil | A61L 2/10 |
| | | | 250/455.11 |
| 2016/0106873 A1 | 4/2016 | Dobrinsky | |
| 2017/0296142 A1* | 10/2017 | Wodecki | A61B 8/4433 |
| 2019/0060495 A1* | 2/2019 | Gil | A61L 2/0047 |
| 2019/0262487 A1* | 8/2019 | Gil | A61L 2/202 |
| 2021/0112647 A1* | 4/2021 | Coleman | H05B 45/12 |
| 2021/0350689 A1* | 11/2021 | Kelly | G08B 21/245 |
| 2022/0313850 A1* | 10/2022 | Baarman | A61L 2/26 |
| 2023/0012506 A1* | 1/2023 | Russ | A61L 2/18 |
| 2023/0138192 A1* | 5/2023 | Wang | G16H 40/63 |
| | | | 705/2 |

FOREIGN PATENT DOCUMENTS

| | | |
|---|---|---|
| WO | WO 2013/106077 | 7/2013 |
| WO | WO 2016/064441 | 4/2016 |
| WO | WO 2017/020028 | 2/2017 |
| WO | 2019008227 | 1/2019 |
| WO | WO 2019/190967 | 10/2019 |

OTHER PUBLICATIONS

U.S. Appl. No. 29/735,235, filed May 19, 2020.
U.S. Appl. No. 17/039,011, filed Sep. 30, 2020.
U.S. Appl. No. 17/020,942, filed Sep. 15, 2020.
U.S. Appl. No. 16/987,514, filed Aug. 7, 2020.
U.S. Appl. No. 17/104,628, filed Nov. 25, 2020.
U.S. Appl. No. 16/987,647, filed Aug. 7, 2020.
U.S. Appl. No. 17/026,417, filed Sep. 21, 2020.
U.S. Appl. No. 17/020,951, filed Sep. 15, 2020.
"Honeywell UV Treatment System," https://aerospace.honeywell.com/en/learn/products/cabin/uv-cabin-system.
U.S. Appl. No. 17/026,435, filed Sep. 21, 2020.
U.S. Appl. No. 17/022,392, filed Sep. 16, 2020.
Extended European Search Report for EP 21178864.1-1202, dated Nov. 5, 2021.
Extended European Search Report for EP 21172799.5, dated Nov. 26, 2021.
Communication pursuant to Article 94(3) EPC for EP 21178864.1-1201, dated Feb. 20, 2024.

* cited by examiner

ULTRAVIOLET LIGHT SANITIZING PACING SYSTEMS AND METHODS

RELATED APPLICATIONS

This application is a continuation-in-part of U.S. patent application Ser. No. 17/020,942, entitled "Ultraviolet Sanitizing Pacing Systems and Methods," filed Sep. 15, 2020, which is hereby incorporated by reference in its entirety, and which, in turn, claims priority benefits from U.S. Provisional Patent Application No. 63/037,630, entitled "Ultraviolet Sanitizing Pacing Systems and Methods," filed Jun. 11, 2020.

This claims priority benefits from U.S. Provisional Patent Application No. 63/021,984, entitled "Portable Sanitizing Systems and Methods," filed May 8, 2020.

This application is also a continuation-in-part of U.S. Design Patent Application No. 29/735,235, entitled "Ultraviolet Wand," filed May 19, 2020, which is hereby incorporated by reference in its entirety.

This application also relates to and claims priority benefits from U.S. Provisional Patent Application No. 63/027,869, entitled "Portable Sanitizing Systems and Methods with Range Guidance," filed May 20, 2020.

This application also relates to and claims priority benefits from U.S. Provisional Patent Application No. 63/037,039, entitled "Systems and Methods for Maintaining Electrical Contact in Relation to an Ultraviolet Lamp," filed Jun. 10, 2020.

This application also relates to and claims priority benefits from U.S. Provisional Patent Application No. 63/067,999, entitled "Ultraviolet Sanitizing Pacing Systems and Methods," filed Aug. 20, 2020.

FIELD OF THE DISCLOSURE

Embodiments of the present disclosure generally relate to sanitizing systems, such as may be used to sanitize structures and areas within vehicles, and more particularly to systems and methods of pacing movement of such sanitizing systems.

BACKGROUND OF THE DISCLOSURE

Vehicles such as commercial aircraft are used to transport passengers between various locations. Systems are currently being developed to disinfect or otherwise sanitize surfaces within aircraft, for example, that use ultraviolet (UV) light.

In order to sanitize a surface of a structure, a known UV light sterilization method emits a broad spectrum UVC light onto the structure. However, UVC light typically takes a significant amount of time (for example, three minutes) to kill various microbes. Further, various microbes may not be vulnerable to UVC light. That is, such microbes may be able to withstand exposure to UVC light.

Also, certain types of microbes may develop a resistance to UVC light. For example, while UVC light may initially kill certain types of microbes, with continued exposure to UVC light over time, the particular species of microbe may develop a resistance to UVC light and able to withstand UVC light exposure.

Further, certain known manual surface treatment devices rely on an operator to perform with high degrees of repeatability to produce a high quality disinfection treatment. However, manual processes tend to vary, and may be difficult to simultaneously maintain a high degree of quality control and efficiency.

SUMMARY OF THE DISCLOSURE

A need exists for a system and a method for efficiently sterilizing surfaces within an internal cabin of a vehicle. Further, a need exists for a mobile, compact, easy-to-use, consistent, reliable, and safe system and method for using UV light to sterilize surfaces within an internal cabin.

With those needs in mind, certain embodiments of the present disclosure provide an ultraviolet (UV) light pacing system including an assembly (such as a wand assembly) including a UV lamp configured to emit UV light to disinfect a component. One or more range light sources are configured to emit ranging light. At least one aspect of the ranging light is altered to provide a visual cue for guiding motion of the assembly to disinfect the component.

In at least one embodiment, the one or more range light sources are secured to the assembly.

As an example, the at least one aspect includes one or more of duration of emission of the ranging light, frequency of emission of the ranging light, color of the ranging light, or intensity of ranging light.

The UV lamp may be configured to emit the UV light having a wavelength between 200 nm-230 nm. For example, the UV light may be emitted at wavelength of 222 nm.

In at least one other embodiment, the UV lamp may be configured to emit the UV light having a wavelength within the UVC spectrum, such as between 230 nm-280 nm. For example, the UV light may be emitted at a wavelength of 254 nm.

In at least one embodiment, a pacing control unit is in communication with the one or more range light sources. The pacing control unit is configured to operate the one or more range light sources to alter the at least one aspect of the ranging light. The assembly may include the pacing control unit.

In at least one embodiment, a pacing database is in communication with the pacing control unit. The pacing database stores surface disinfection data for one or more surfaces of one or more components.

In at least one embodiment, the pacing control unit shows surface disinfection information regarding the surface disinfection data for the component on a display of a user device.

In at least one embodiment, the pacing database further stores map data regarding at least one map of an environment. The at least one map divides at least a portion of the environment into a plurality of zones. Each of the plurality of zones is associated with respective surface disinfection data.

In at least one embodiment, the UV light pacing system also includes a user device including a display and a selector. For example, the selector is configured to allow selection of a time period for at least a portion of the visual cue. The assembly may include the user device.

In at least one embodiment, a navigation sub-system is configured to track a location of the assembly within an environment. As an example, the pacing control unit is in communication with the assembly and the navigation subsystem. As a further example, the pacing control unit, based on the location of the assembly in relation to the component within the environment, automatically determines surface disinfection data for the surface of the component.

In at least one embodiment, an augmented reality subsystem is in communication with the assembly and the pacing control unit. As an example, the pacing control unit automatically shows one or both of surface disinfection data regarding the surface of the component or one or more visual indications for moving the assembly to disinfect various surfaces on a portion of the augmented reality sub-system as an operator moves through an environment.

In at least one embodiment, the assembly further includes a cover that covers the UV lamp. The cover is one of a wire mesh screen or a stamped or laser cut metal sheet with formed apertures.

Certain embodiments of the present disclosure provide an ultraviolet (UV) light pacing method, including emitting ranging light from one or more range light sources of an assembly having a UV lamp configured to emit UV light to disinfect a component; and altering at least one aspect of the ranging light to provide a visual cue for guiding motion of the assembly to disinfect the component.

Certain embodiments of the present disclosure provide an ultraviolet (UV) light pacing system that includes an assembly including a UV lamp configured to emit UV light to disinfect a component. A cover is over, under, around, or the like (that is, covers) the UV lamp. The cover is one of a wire mesh screen or a stamped or laser cut metal sheet with formed apertures.

DETAILED DESCRIPTION OF THE DISCLOSURE

Figure 1:
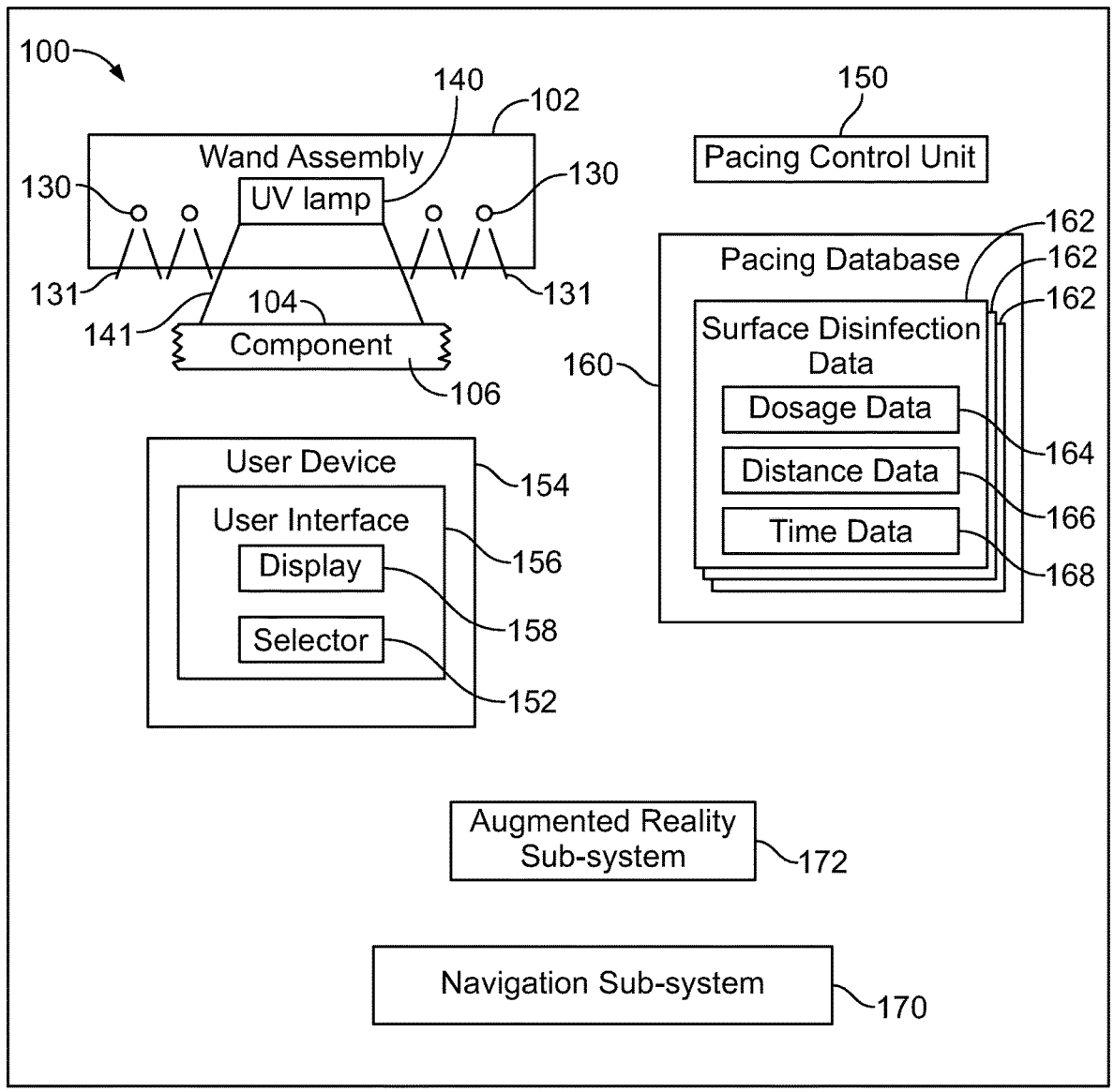
FIG. 1 illustrates a schematic block diagram of a UV light pacing system, according to an embodiment of the present disclosure.

The foregoing summary, as well as the following detailed description of certain embodiments will be better understood when read in conjunction with the appended drawings. As used herein, an element or step recited in the singular and preceded by the word "a" or "an" should be understood as not necessarily excluding the plural of the elements or steps. Further, references to "one embodiment" are not intended to be interpreted as excluding the existence of additional embodiments that also incorporate the recited features. Moreover, unless explicitly stated to the contrary, embodiments "comprising" or "having" an element or a plurality of elements having a particular condition can include additional elements not having that condition.

Certain embodiments of the present disclosure provide a sanitizing system and method that includes an ultraviolet (UV) lamp (such as an excimer lamp having one or more light emitting devices, such as light emitting diodes, bulbs, and/or the like) that emits UV light in a far UV light spectrum, such as at a wavelength of 222 nm, which neutralizes (such as kills) microbes (for example, viruses and bacteria), while posing no risk to humans. Optionally, the UV lamp emits the UV light in the UVC spectrum, such as at a wavelength of 254 nm. The UV lamp may be used within an internal cabin to decontaminate and kill pathogens. The UV lamp may be used in a portable sanitizing system or a fixed sanitizing system. For example, operating the UV lamp to emit sanitizing UV light having a wavelength within the far UV spectrum or UV spectrum may be used with a portable system or a fixed system.

The effectiveness of a UV sanitation system is determined by a dose (such as in mJ/cm2) required to kill a targeted pathogen. The dose is a function of an optical power of the UV light (in watts) and the time of exposure. Certain embodiments of the present disclosure provide a pacing guidance system that provides a user with a cue (such as a visual cue, such as via altered ranging lighting) allowing them to provide a correct amount of time for sanitizing UV light exposure. Embodiments of the present disclosure allow a user to pace movement of a wand assembly during sanitation to ensure that a correct dose of UV light for disinfecting has been delivered. Embodiments of the present disclosure guide the user according to a required irradiation dose and/or a specific item or items being sanitized.

Certain embodiments of the present disclosure provide a method of pacing UV disinfection of a predetermined surface. The method includes calculating a wand speed, and loading the speed into a computer program. The program provides visual cues (such as altered ranging lighting) regarding a rate at which to move the wand, and may provide feedback so that the user can maintain said rate.

In at least one embodiment, the visual cues are altered light emitted from range light sources. For example, the range light sources emit ranging light onto a surface of a component that is being sanitized. The ranging light can be alternately deactivated and activated to provide a visual cue as to pacing of the wand assembly over the surface of the component. For example, the ranging light can blink at predetermined intervals to provide a timing cue for moving the wand assembly in relation to the surface of the component. As another example, the color of the ranging light can be changed at predetermined intervals to provide the timing cue. As another example, the intensity of the ranging light can be changed at predetermined intervals to provide the timing cue.

The wand speed is calculated by entering known parameters such as range to surface, irradiance of wand, disinfection energy required to sanitize the surface, wand length, and wand width to conduct calculations for time required to disinfect surfaces.

The speed of the UV wand movement determines the time of exposure, and typically determines whether or not the correct dose required to disinfect a surface is achieved. For example, a surface of a component may not be effectively sanitized if the UV wand is moved too quickly in relation to the surface. Certain embodiments of the present disclosure provide a UV light pacing system that allows a user to pace the movement of a UV wand assembly via light pulses from the ranging lights (such as LED range light sources).

In at least one embodiment, the UV light pacing system guides UV disinfection of an area being sanitized by dividing the area into subzones that are sanitized (for example, disinfected) through a series of time distinct passes (such as three, four, five, or six second passes) with the UV wand assembly, regardless of length. The pace of the UV wand movement is guided by a pulse frequency of the range light sources.

Certain embodiments of the present disclosure provide a system for pacing UV disinfection on a predetermined surface, including a UV wand assembly having range light sources that emit ranging light onto a surface of a component. The range light sources are controlled to emit the ranging light to pulse at a particular frequency, such as at predetermined intervals, to provide visual cues to pace the UV cleaning speed. A pacing control unit, such as an integrated circuit, controls the pulse time. In at least one embodiment, an area to be disinfected is divided into predefined zones based on known dimensions, such that each subzone is disinfected with one or more set time passes, such as one or more three second passes, of the UV wand assembly, regardless of length.

Certain embodiments of the present disclosure provide a method for disinfecting a surface of a component, including selecting a subzone to be disinfected, determining a number of set time passes required to disinfect the subzone, selecting an appropriate time period on a selector, sweeping a UV wand assembly across the subzone based on pulsating range light sources, and repeating the sweeping motion for a number of determined passes.

Certain embodiments of the present disclosure provide a system and a method for pacing disinfection of a surface using a portable UV wand assembly to ensure a correct UV irradiation dose has been delivered thereto. The system and method work in conjunction with range light sources to provide a visual cue to a user to provide the correct amount of time for sweeping the UV wand assembly across a predetermined subzone.

FIG. 1 illustrates a schematic block diagram of a UV light pacing system 100, according to an embodiment of the present disclosure. The UV light pacing system 100 includes an assembly, such as a wand assembly 102 having one or more range light sources 130 and a UV lamp 140. Alternatively, the range light sources 130 may be separate from the wand assembly 102, such as on a separate housing that is used in conjunction with the wand assembly 102. The range light sources 130 are configured to emit ranging light 131, such as onto a surface 104 of a component 106 to be disinfected. The UV lamp 140 is configured to emit UV light 141 onto the surface 104 to disinfect the surface 104. Optionally, the assembly may be other than a wand assembly. For example, the assembly may be a part of a system having an arm, boom, disc, shield, or the like including the UV lamp 140.

As described herein, the UV light pacing system 100 includes the wand assembly 102 including the UV lamp 140, which is configured to emit UV light 141 to disinfect the surface 104 of the component 106. One or more range light sources 130 are configured to emit ranging light 131. At least one aspect (for example, duration and/or frequency of emission, color of light, intensity of light, or the like) of the ranging light 131 is altered to provide a visual cue for guiding motion of the wand assembly 102 to disinfect the surface 104 of the component 106. In at least one embodiment, the range light sources 130 are secured to the wand assembly 102.

Further, as described herein, a UV light pacing method includes emitting ranging light from the one or more range light sources 130 of the wand assembly 102, which has the UV lamp 140 that is configured to emit UV light 141 to disinfect the surface 104 of the component 106. The method also includes altering at least one aspect (for example, duration and/or frequency of emission, color of light, intensity of light, or the like) of the ranging light 141 to provide a visual cue for guiding motion of the wand assembly 102 to disinfect the surface 104 of the component 106.

In at least one embodiment, the range light sources 130 can be light emitting diodes (LEDs). The range light sources 130 emit the ranging light 131 to provide a visual indication of a proper distance (that is, a range) between the wand assembly 102 and the surface 104 to effectively disinfect the surface 104. In at least one embodiment, the wand assembly 102 includes multiple range light sources 130. For example, the wand assembly 102 includes at least one pair of associated range light sources 130. In at least one other embodiment, the wand assembly 102 includes a single range light source 130.

The UV lamp 140 emits the UV light 141 at a predetermined wavelength. For example, the UV lamp 140 emits the UV light 141 within a far UV spectrum. For example, the UV lamp 140 emits the UV light 141 at a wavelength of 222 nm. As another example, the UV lamp 140 emits the UV light 141 within the UVC spectrum.

A pacing control unit 150 is in communication with the range light sources 130, such as through one or more wired or wireless connections. In at least one embodiment, the pacing control unit 150 is within the wand assembly 102. That is, the wand assembly 102 includes the pacing control unit 150. In at least one other embodiment, the pacing control unit 150 is remote from the wand assembly 102, such as within a computing device, such as a desktop or laptop computer, a handheld smart device (such as a smart phone or tablet), or the like.

The pacing control unit 150 is configured to operate the one or more range light sources 130 to alter the at least one aspect of the ranging light 131. In order to pace or otherwise guide motion of the wand assembly 102 in relation to the component 106 to properly and effectively disinfect the surface 104, the pacing control unit 150 controls the range light sources 130 to alter the ranging light 131. The altered light provides a visual cue that guides a pacing speed of motion of the wand assembly 102 in relation to the component 106. For example, the pacing control unit 150 can selectively deactivate the range light sources 130 at predetermined times for a predetermined time period to provide a blinking and/or pulsing effect of the ranging light 131. As an example, when the wand assembly 102 is activated so that the UV lamp 140 emits the UV light 141, the pacing control unit 150 provides a timer that initially deactivates the ranging light 131 at an initial time, thereby providing an initial blink or deactivation, reactivates the ranging light for a set period (such as 1 or 1.5 seconds), after which the pacing control unit 150 again deactivates the ranging light, and so on. In this manner, the pacing control unit 150 operates the range light sources 130 to provide a series of light pulses at regular, predetermined intervals (such as emitted onto the surface) that provides a visual timing cue to an operator of the wand assembly 102. For example, if the time interval between a first deactivation of the range light sources 130 (for example, a first blink) and a second deactivation of the range light sources 130 is one second, the operator is able to determine that each blink represents a second. As such, if an effective time for moving the wand assembly 102 in relation to the surface 104 to disinfect the surface is 3 seconds over a length of the surface 104, the operator determines that the wand assembly 102 is to be moved over the length of the surface 104 for at least three additional deactivations after the initial deactivation (totaling three pulses of ranging light 131 on the surface 104. Optionally, the time for each pulse of ranging light 131 (that is, the time of activation of the ranging light 131 between deactivations (for example, blinks) may be greater or less than 1 second. For example, the time for each pulse can be 1.5 seconds. As another example, the time for each pulse can be 0.5 seconds. As another example, the time for each pulse can be 2 seconds.

In at least one embodiment, the operator can select the time (for example, 0.5 second interval, 1 second interval, 1.5 second interval, 2 second interval, or the like) for each pulse via a selector 152 of a user device 154. That is, the selector 152 is configured to allow selection of a time period for at least a portion of the visual cue, such as a time period for a pulse of the ranging light 131. The user device 154 includes a user interface 156 that includes the display 158 and the selector 152. In at least one embodiment, the display 158 and the selector 152 are part of a touchscreen interface. The selector 152 can be a virtual button, slide, switch, dial, and/or the like. Optionally, the selector 152 can be a physical button, slide, switch, dial, and/or the like.

In at least one embodiment, the user device 154 is a computing device, such as a personal or laptop computer, a handheld smart device (such as a smart phone or smart tablet), or the like. In at least one other embodiment, the wand assembly 102 includes the user device 154. For example, the wand assembly 102 can include a handle having the user device 154. Alternatively, the UV light pacing system 100 does not include the user device 154.

Optionally, instead of the visual cues being light pulses, the color of the ranging light can be changed at predetermined intervals to provide the timing cues. As another example, the intensity of the ranging light can be changed at predetermined intervals to provide the timing cue.

In at least one embodiment, the UV light pacing system 100 includes a pacing database 160 in communication with the pacing control unit 150 and/or the user device 154, such as through one or more wired or wireless connections. In at least one embodiment, the pacing database 160 is within the wand assembly 102. For example, the wand assembly 102 may include the pacing database 160. In at least one other embodiment, the pacing database 160 is remote from the wand assembly 102.

The pacing database 160 stores surface disinfection data 162 for one or more surfaces of one or more components. The surface disinfection data 162 includes information regarding a dosage of UV light, a distance (including range between the wand assembly 102 and the surface 104, and/or the length of the surface 104), and a time for disinfection via the UV light 141. For example, the surface disinfection data 162 includes dosage data 164 regarding the dosage of UV light to disinfect the surface 104, distance data 166 regarding the distance in relation to the wand assembly 102 and the surface 104 to disinfect the surface 104, and time data 168 regarding the time for disinfection via the UV light 141 emitted by the UV lamp 140. The pacing database 160 may store surface disinfection data 162 for a plurality of surfaces 104 for a plurality of components 106. For example, the surfaces 104 may be one or more zones or sub-zones within an internal cabin of a vehicle, such as a commercial aircraft.

In at least one embodiment, the surface disinfection data 162 may also differ for different pathogens to be killed, eliminated, neutralized, or the like during a disinfection process. For example, the surface disinfection data 162 for Covid-19 may have a particular dosage data 164, distance data 166, and time data 168 for a particular surface 104 that differs from a dosage data 164, distance data 166, and time data 168 for a different pathogen, such as influenza, salmonella, MERS, or the like.

During operation, an operator of the wand assembly 102 consults the surface disinfection data 162 for a particular surface 104 to be sanitized to determine proper pacing of the wand assembly 102 in relation to the surface 104. The surface disinfection data 162 can be shown in a guidebook. As another example, the operator can select a particular surface to be disinfected through the selector 152 of the user interface 156, and the surface disinfection data 162 can be shown on the display 158. For example, the operator can select a particular surface of a component via the user interface 156 to show the surface disinfection data 162 for that particular surface.

In at least one other embodiment, the UV light pacing system 100 includes a navigation sub-system 170 that is configured to track the location of the wand assembly 102 within an environment, such as within an internal cabin of a vehicle. The navigation sub-system 170 can be a global position system (GPS) sub-system, a localized three dimensional tracking sub-system, or the like. The navigation sub-system 170 is in communication with the pacing control unit 150 through one or more wired or wireless connections. As the wand assembly 102 is moved through the environment, the navigation sub-system 170 tracks the location of the wand assembly 102 in relation to various components 106 within the environment. The pacing control unit 150 monitors the location of the wand assembly 102 within the environment, via signals received from the navigation sub-system 170. Based on the position of the wand assembly 102 in relation to the various components 106 within the environment, the pacing control unit 150 may automatically determine and selectively show the surface disinfection data 162 for the components 106 proximate to the wand assembly 102. In this manner, the pacing control unit 150 may automatically show surface disinfection data 162 for different components 106 via the user interface 156 as the wand assembly 102 moves proximate (such as within 2 feet or less) the various components. Alternatively, the UV light pacing system 100 may not include the navigation sub-system 170.

In at least one embodiment, the UV light pacing system 100 includes a an augmented reality sub-system 172. The augmented reality sub-system 172 can include an augmented reality article, such as headset, glasses, or the like) in communication with an augmented reality control unit. The augmented reality sub-system 172 is in communication with the wand assembly 102 and the pacing control unit 150, such as through one or more wired or wireless connections.

In operation, the operator wears the augmented reality article, and a map of the environment may be shown thereon and registered to and/or superimposed onto the actual environment. As the operator moves through the environment, the pacing control unit 150 may show surface disinfection data 162 for particular components on the augmented reality article. For example, the pacing control unit 150 may match actual components to those of a stored map of the environment. As such, the pacing control unit 150 may automatically show the surface disinfection data 162 and/or visual indications for moving the wand assembly 102 to disinfect various surfaces as the operator moves through the environment. Alternatively, the UV light pacing system 100 may not include the augmented reality sub-system 172.

As used herein, the term "control unit," "central processing unit," "CPU," "computer," or the like may include any processor-based or microprocessor-based system including systems using microcontrollers, reduced instruction set computers (RISC), application specific integrated circuits (ASICs), logic circuits, and any other circuit or processor including hardware, software, or a combination thereof capable of executing the functions described herein. Such are exemplary only, and are thus not intended to limit in any way the definition and/or meaning of such terms. For example, the pacing control unit 150 may be or include one or more processors that are configured to control operation, as described herein.

The pacing control unit 150 is configured to execute a set of instructions that are stored in one or more data storage units or elements (such as one or more memories), in order to process data. For example, the pacing control unit 150 may include or be coupled to one or more memories. The data storage units may also store data or other information as desired or needed. The data storage units may be in the form of an information source or a physical memory element within a processing machine.

The set of instructions may include various commands that instruct the pacing control unit 150 as a processing machine to perform specific operations such as the methods and processes of the various embodiments of the subject matter described herein. The set of instructions may be in the form of a software program. The software may be in various forms such as system software or application software. Further, the software may be in the form of a collection of separate programs, a program subset within a larger program, or a portion of a program. The software may also include modular programming in the form of object-oriented programming. The processing of input data by the processing machine may be in response to user commands, or in response to results of previous processing, or in response to a request made by another processing machine.

The diagrams of embodiments herein may illustrate one or more control or processing units, such as the pacing control unit 150. It is to be understood that the processing or control units may represent circuits, circuitry, or portions thereof that may be implemented as hardware with associated instructions (e.g., software stored on a tangible and non-transitory computer readable storage medium, such as a computer hard drive, ROM, RAM, or the like) that perform the operations described herein. The hardware may include state machine circuitry hardwired to perform the functions described herein. Optionally, the hardware may include electronic circuits that include and/or are connected to one or more logic-based devices, such as microprocessors, processors, controllers, or the like. Optionally, the pacing control unit 150 may represent processing circuitry such as one or more of a field programmable gate array (FPGA), application specific integrated circuit (ASIC), microprocessor(s), and/or the like. The circuits in various embodiments may be configured to execute one or more algorithms to perform functions described herein. The one or more algorithms may include aspects of embodiments disclosed herein, whether or not expressly identified in a flowchart or a method.

As used herein, the terms "software" and "firmware" are interchangeable, and include any computer program stored in a data storage unit (for example, one or more memories) for execution by a computer, including RAM memory, ROM memory, EPROM memory, EEPROM memory, and non-volatile RAM (NVRAM) memory. The above data storage unit types are exemplary only, and are thus not limiting as to the types of memory usable for storage of a computer program.

Figure 2:
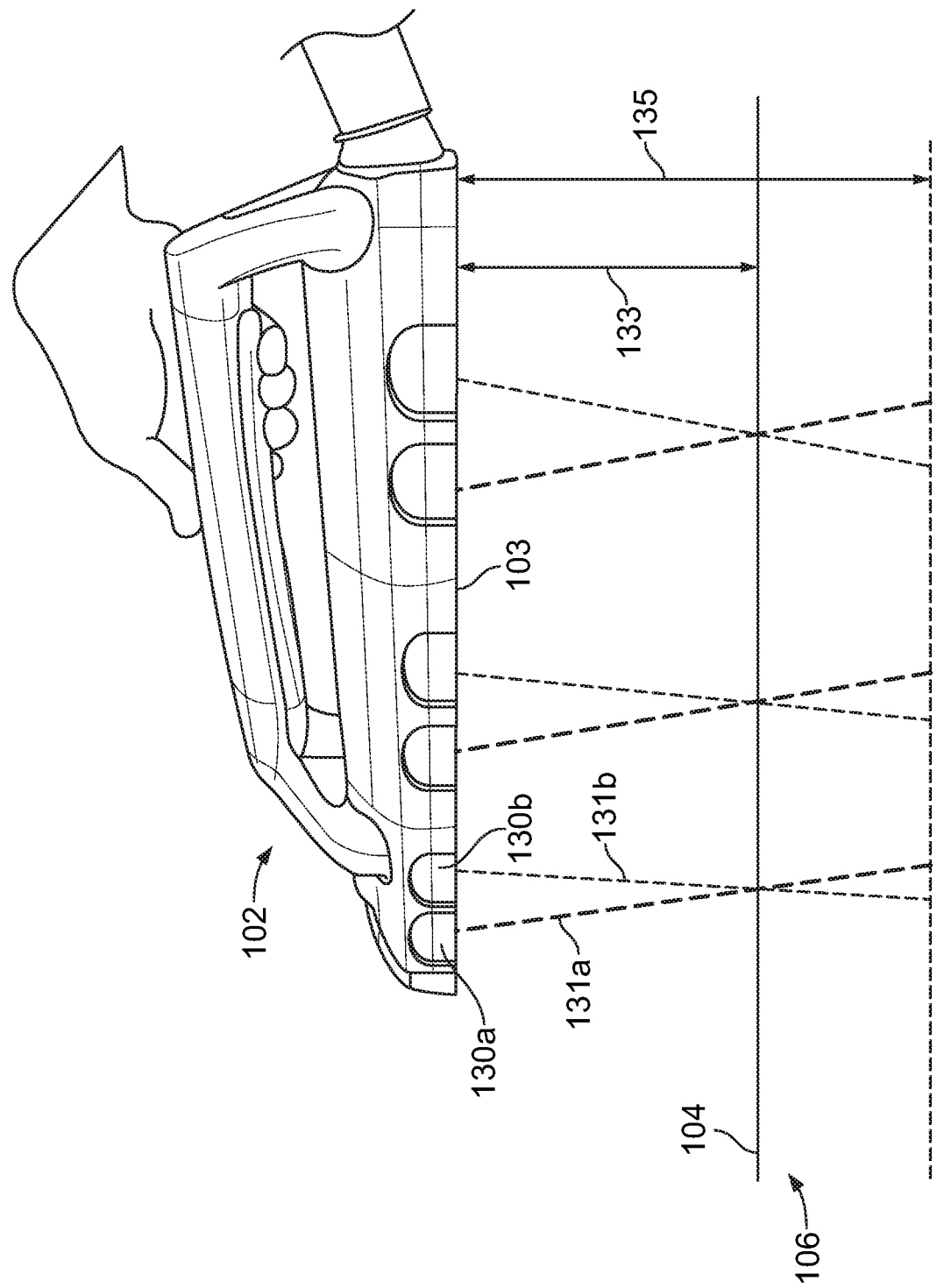
FIG. 2 illustrates a perspective view of a wand assembly in relation to a surface of a component, according to an embodiment of the present disclosure.
Figure 3A:
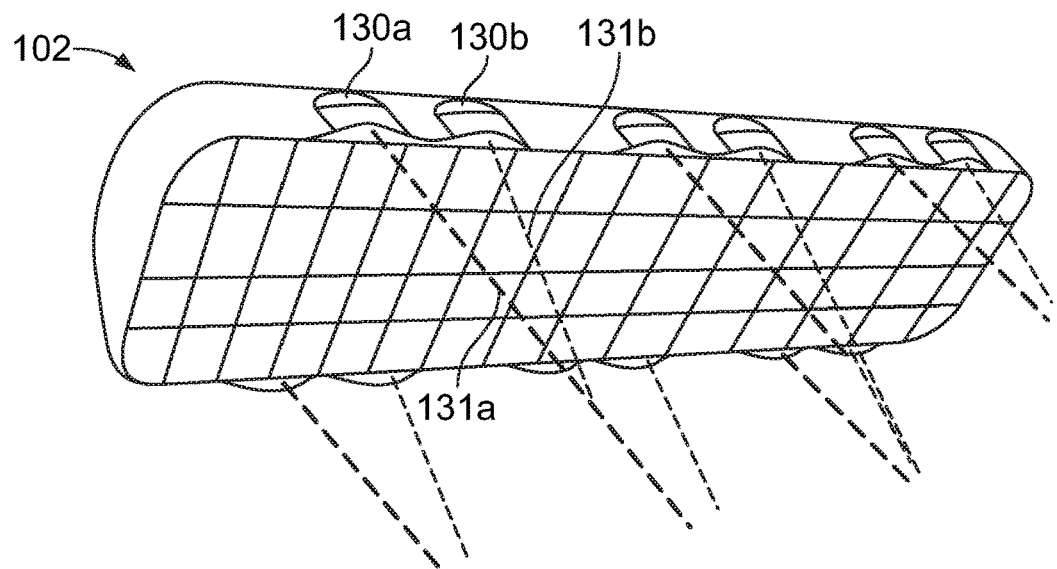
FIG. 3A illustrates a perspective bottom view of the wand assembly.
Figure 4:
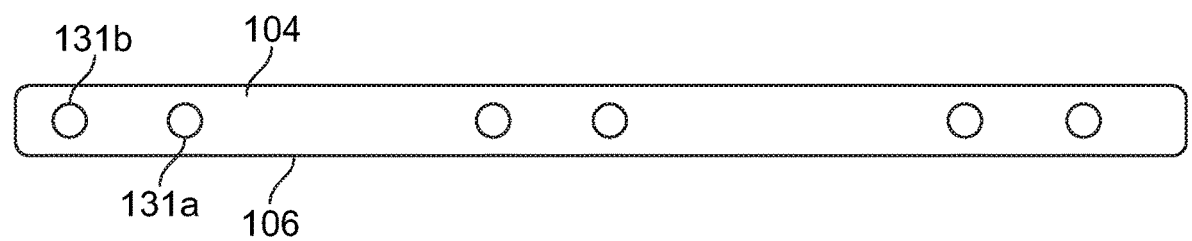
FIG. 4 illustrates a front view of the surface of the component when the wand assembly is outside of a disinfection range, according to an embodiment of the present disclosure.
Figure 5:
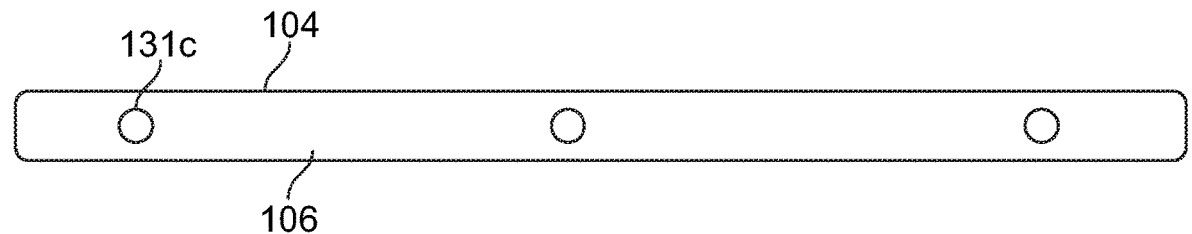
FIG. 5 illustrates a front view of the surface of the component when the wand assembly is at the disinfection range, according to an embodiment of the present disclosure.

FIG. 2 illustrates a perspective view of the wand assembly 102 in relation to the surface 104 of the component 106, according to an embodiment of the present disclosure. FIG. 3A illustrates a perspective bottom view of the wand assembly 102. FIG. 4 illustrates a front view of the surface 104 of the component 102 when the wand assembly 102 is outside of a disinfection range, according to an embodiment of the present disclosure. FIG. 5 illustrates a front view of the surface 104 of the component 106 when the wand assembly 102 is at the disinfection range, according to an embodiment of the present disclosure.

Referring to FIGS. 2-5, a range light source 130a emits the ranging light 131a, such as a first light marker, at a first color, and the range light source 130b emits the ranging light 131b, such as a second light marker, at a second color. The ranging light 131a and the ranging light 131b converge at a predetermined disinfection range 133. For example, the disinfection range 133 may be 5 inches or less between the bottom 103 of the wand assembly 102 and the surface 104. The ranging light 131a and 130b diverge at a distance 135 outside of the disinfection range 133.

On the surface 104, the ranging lights 130a and 130b provide visual cues as to the correct distance for disinfection. For example, as shown in FIG. 4, the ranging lights 130a and 130b are separated from one another, thereby indicating that the wand assembly 102 is outside of the disinfection range 133. In contrast, as shown in FIG. 5, the ranging lights 130a and 130b are at an overlapping convergence 130c, thereby indicating that the wand assembly 102 is at or otherwise within the disinfection range 133.

Referring to FIGS. 1-5, the range light sources 130 provide visual cues for the disinfection range 133, as well as timing for movement (for example, pacing) of the wand assembly 102 to disinfect the surface 104. For example, the pacing control unit 150 alters one or more aspects of the ranging light 131, such as selective deactivation/activation, color, intensity, and/or the like.

Figure 3B:
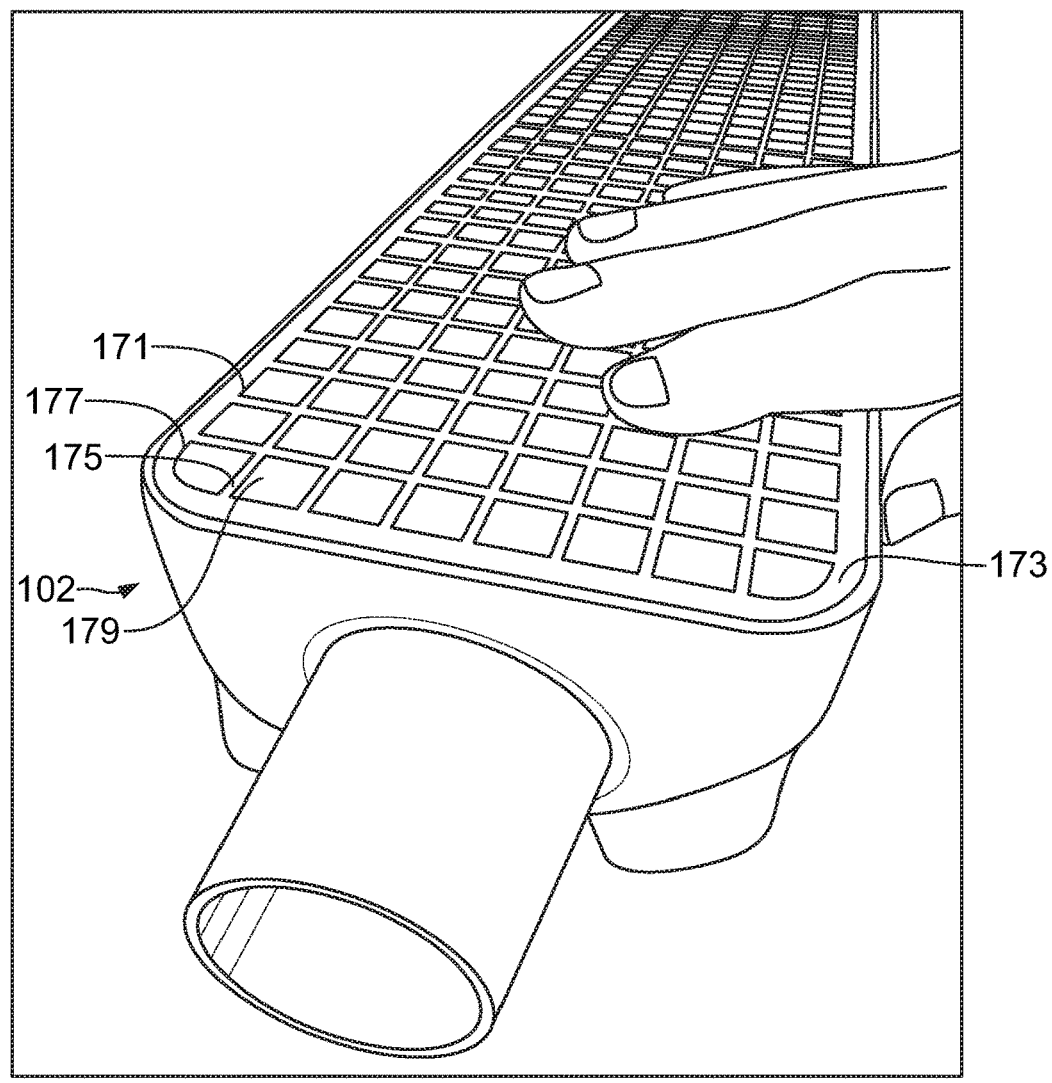
FIG. 3B illustrates a perspective bottom view of the wand assembly, according to an embodiment of the present disclosure.

FIG. 3B illustrates a perspective bottom view of the wand assembly 102, according to an embodiment of the present disclosure. In at least one embodiment, the wand assembly 102 includes a cover 171 on a bottom end. The cover 171 is below the UV lamp 140 (shown in FIG. 1), and is configured to allow UV light emitted from the UV lamp 140 to pass therethrough.

As shown, the cover 171 can be a mesh screen 173 including a plurality of longitudinal beams 175 that intersect a plurality of cross beams 177, thereby forming a plurality of light passages 179 therebetween. The mesh screen 173 may be a wire mesh that covers the UV lamp 140 within the wand assembly 102.

In at least one embodiment, the cover 171 is a stamped or laser cut stainless steel sheet with formed apertures (that is, the light passages 179). The apertures may be rectangular or square shaped as shown in FIG. 3B.

It has been found that the cover 171 formed as a metal mesh screen or stamped sheet of metal, as described herein, provides shielding from electromagnetic interference (EMI). For example, the cover 171 protects the UV lamp 140 from EMI that may be generated outside of the wand assembly 102. Further, the cover 171 eliminates, minimizes, or otherwise reduces a potential of EMI generated within the wand assembly 102 from passing out of the wand assembly 102.

The cover 171 shown and described with respect to FIG. 3B can be used with any of the wand assemblies shown and described herein.

Figure 6:
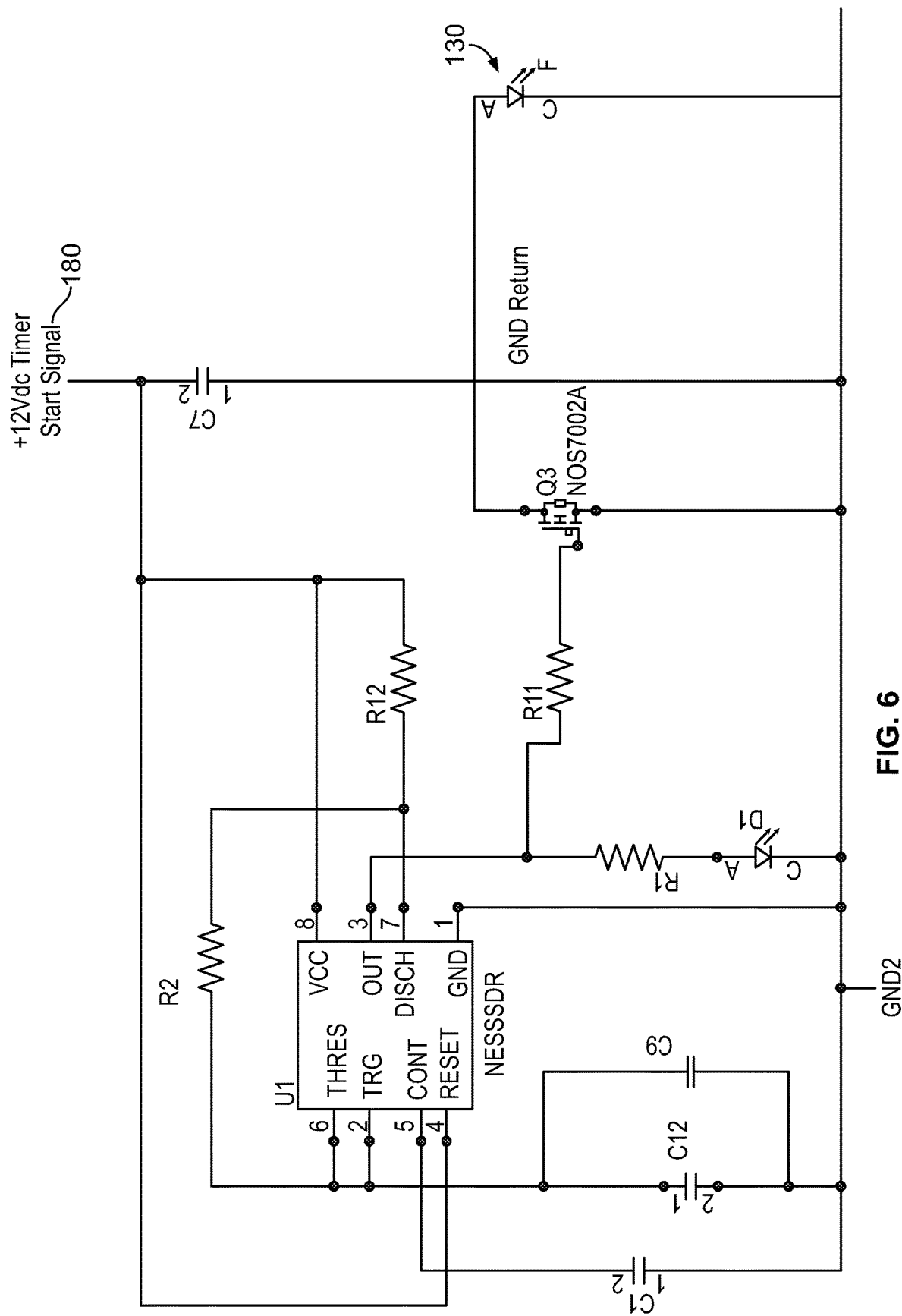
FIG. 6 illustrates an exemplary circuit diagram of range light sources of a wand assembly, according to an embodiment of the present disclosure.

FIG. 6 illustrates an exemplary circuit diagram of the range light sources 130 of the wand assembly 102 (shown in FIG. 1, for example), according to an embodiment of the present disclosure. Referring to FIGS. 1 and 6, the pacing control unit 150 outputs a timer start signal 180 to initiate the selective deactivation and activation of the range light sources 130 to provide the distinct pulses of ranging light 131 to provide a visual cue to an operator for timing a speed of motion of the wand assembly 102 in relation to the surface 104. The circuit shown in FIG. 6 is merely exemplary. The range light sources 130 may include or be part of different circuits.

Figure 7:
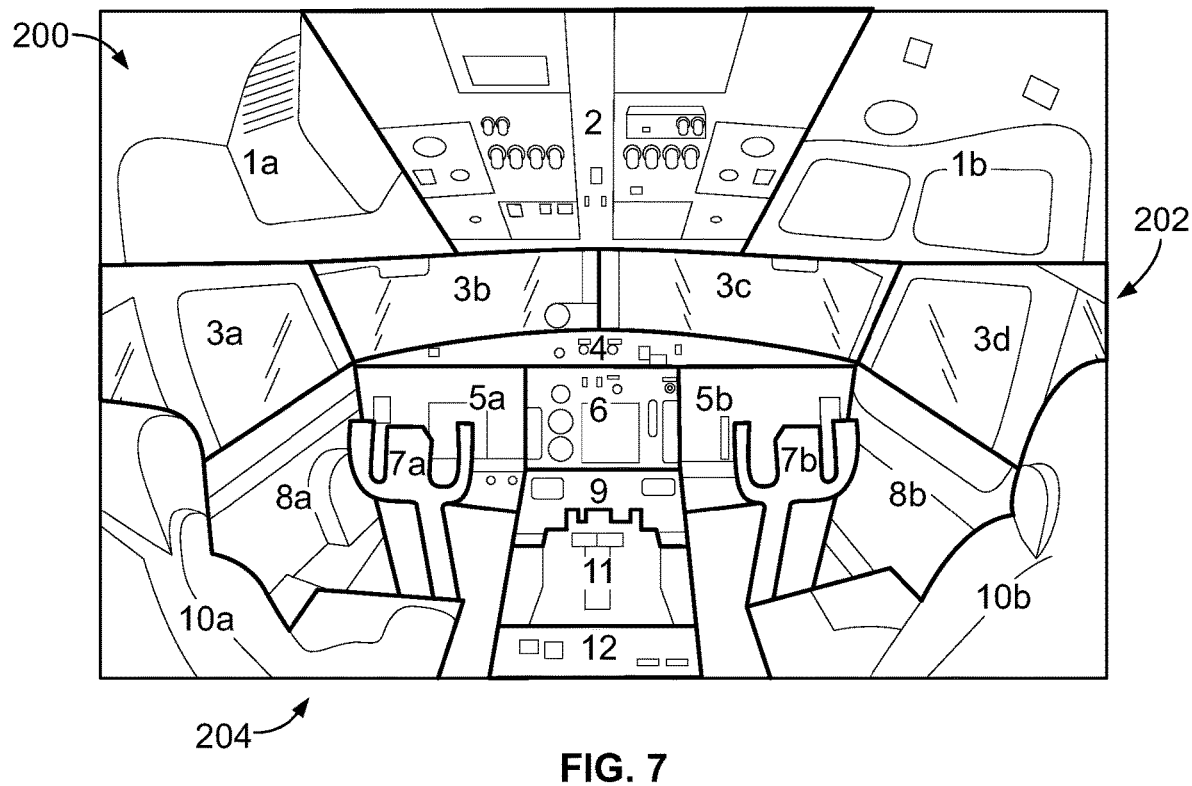
FIG. 7 illustrates a map of an interior of a flight deck of an aircraft, according to an embodiment of the present disclosure.
Figure 8:
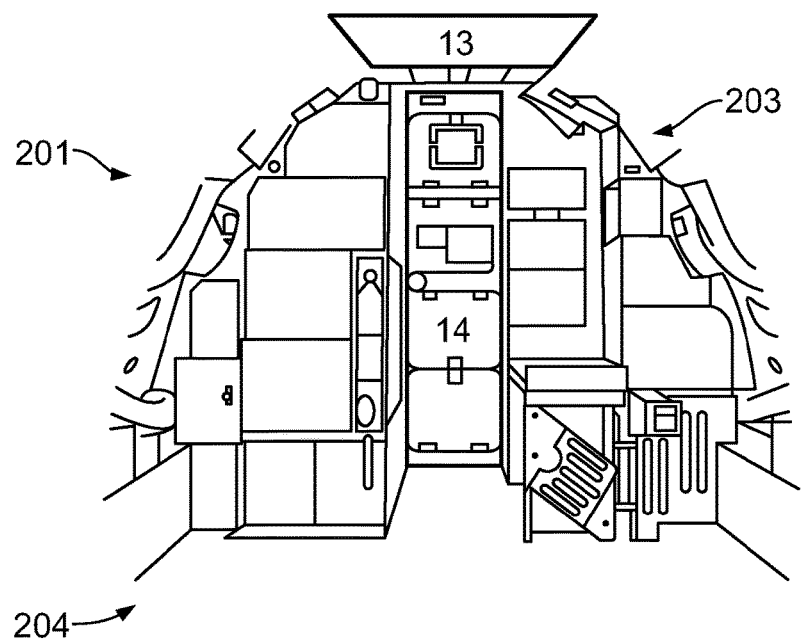
FIG. 8 illustrates a map of an exterior of the flight deck of the aircraft, according to an embodiment of the present disclosure.

FIG. 7 illustrates a map 200 of an interior 202 of a flight deck 204 of an aircraft, according to an embodiment of the present disclosure. FIG. 8 illustrates a map 201 of an exterior 203 of the flight deck 204 of the aircraft, according to an embodiment of the present disclosure. Referring to FIGS. 7 and 8, the flight deck 204 is an example of an environment that is to be disinfected by the wand assembly 102 (shown in FIG. 1). In at least one embodiment, the maps 200 and 201 are stored as map data within the pacing database 160 (shown in FIG. 1), for example.

The maps 200 and 201 divide the flight deck 204 into a plurality of zones and/or subzones. Each of the zones and/or subzones is associated with particular surface disinfection data 162 (shown in FIG. 1) that provided information for disinfecting each zone and/or subzone.

As examples, the zones include overhead lining 1a and 1b, overhead panel 2, windows 3a, 3b, 3c, and 3d, glareshield panel 4, instruments panels 5a and 5b, center instrument panel 6, steering columns 7a and 7b, sidewall liners 8a and 8b, electronic panel 9, seats 10a and 10b, control stand 11, electronic panel 12, overhead panel 13 and flight compartment door 14. Each of the zones can be further divided into subzones.

The zones and environment shown in FIGS. 7 and 8 are merely exemplary. The maps 200 and 201 can be associated with various different environments having different zones and subzones than shown. For example, the maps 200 and/or 201 may be associated with an internal cabin of a different vehicle, an interior space within a building, or the like.

Referring to FIGS. 1, 7, and 8, in at least one embodiment, a method for disinfecting various surfaces within the aircraft includes selecting a surface associated with one of the zones to be disinfected, such as through the user device 154. Next, the pacing control unit 150 retrieves the surface disinfection data 162 for the selected zone from the pacing database 160. The surface disinfection data 162 provides instructions for disinfecting the selected zone, such as with respect to a number of sweeps by the wand assembly 102 of the surface 104 and a time for each sweep, as guided by the visual cues from the range light sources 130. The instructions may be shown on the display 158, for example. The wand assembly 102 is then operated and moved according to the instructions.

In at least one embodiment, each of the zones may be based on known dimensions. One or more of the zones may be further divided into subzones. In at least one embodiment, each subzone may be disinfected by one or more 3 second passes of the wand assembly 102, regardless of length. The number of passes may be determined by the size of the subzone. Additionally, other areas of the aircraft may be divided into similar subzones.

Figure 9:
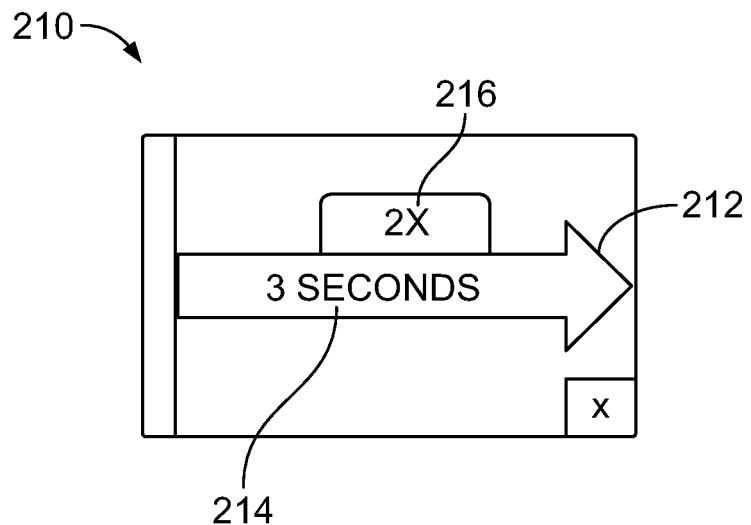
FIG. 9 illustrates a front view of a disinfecting instruction for a surface associated with a zone of a map, according to an embodiment of the present disclosure.

FIG. 9 illustrates a front view of a disinfecting instruction 210 for a surface associated with a zone of a map, according to an embodiment of the present disclosure. Referring to FIGS. 1 and 9, in at least one embodiment, surface disinfection information, which represents the surface disinfection data 162, includes the disinfecting instruction 210 for the surface 104 to be disinfected. The surface 104 of the component 106 is associated with the zone. Optionally, the disinfecting instruction may be for the surface, whether or not associated with a zone of a map.

The disinfecting instruction 210 may be shown on the display 158 of the user device 154, for example. As another example, the disinfecting instruction 210 may be shown on the augmented reality article of the augmented reality subsystem 172. As another example, the disinfecting instruction 210 may be shown on a disinfecting guidebook.

As shown, the disinfecting instruction 210 includes a direction 212 of sweep of the wand assembly in relation to the surface, a time 214 of the sweep over a length of the surface, and a number 216 of sweeps. As shown in FIG. 9, the disinfecting instruction 210 indicates a sweep from left to right for three seconds to be performed twice. The disinfecting instruction 210 shown in FIG. 9 is merely exemplary. The disinfecting instruction 210 may include a different direction, a different time, and a different number of sweeps that shown. The timing of the sweep is guided by the visual cues as provided by the pacing control unit 150 altering one or more aspects of the range light sources 130 (such as, for example, selective deactivation/activation to provide pulses of light, color changes of the light, intensity changes of the light, and/or the like).

Figure 10:
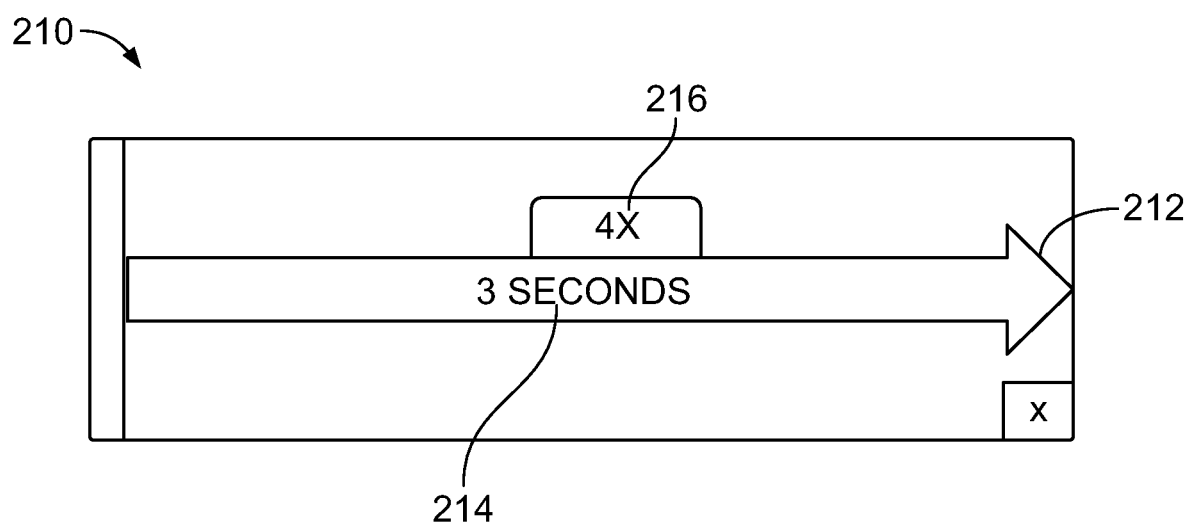
FIG. 10 illustrates a front view of a disinfecting instruction for a surface associated with a zone of a map, according to an embodiment of the present disclosure.

FIG. 10 illustrates a front view of a disinfecting instruction 210 for a surface associated with a zone of a map, according to an embodiment of the present disclosure. The disinfecting instruction 210 shown in FIG. 10 is merely exemplary. As shown in FIG. 10, the disinfecting instruction 210 indicates a sweep from left to right for three seconds to be performed four times.

Referring to FIGS. 7-10, each of the zones of the maps 200 and 201 is associated with surface disinfection data 162, represented, at least in part, by a disinfecting instruction 210. The surface disinfection data 162 for at least two of the zones may differ. As each zone is selected for disinfecting, such as via the user device 154, the disinfecting instruction 210 for the selected zone may be shown on the display 158. Optionally, the disinfecting instructions 210 may be audio signals broadcast through a speaker of the user device 154.

Figure 11:
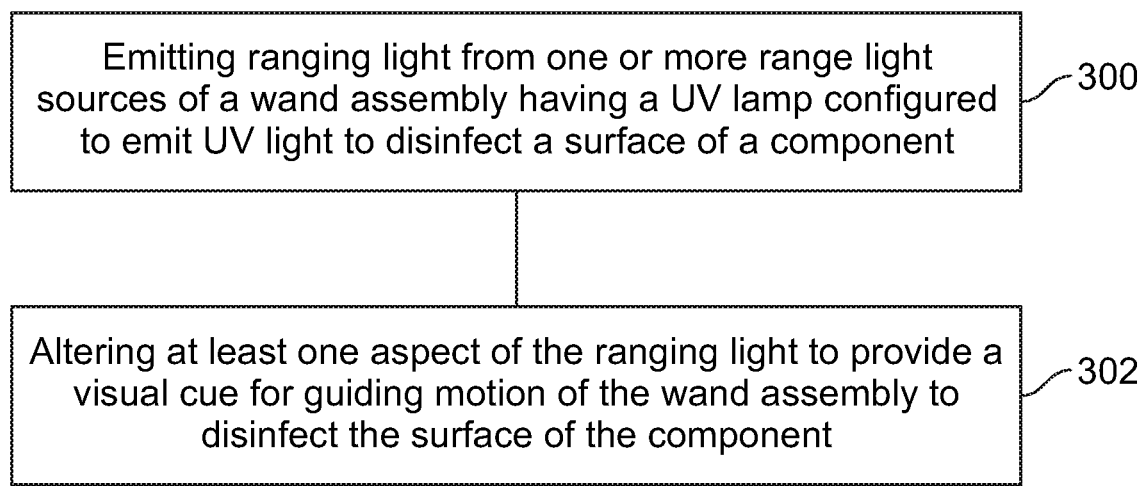
FIG. 11 illustrates a flow chart of a UV light pacing method, according to an embodiment of the present disclosure.

FIG. 11 illustrates a flow chart of a UV light pacing method, according to an embodiment of the present disclosure. The UV light pacing method includes emitting, at 300, ranging light from one or more range light sources of a wand assembly having a UV lamp configured to emit UV light to disinfect a surface of a component; and altering, at 302, at least one aspect of the ranging light to provide a visual cue for guiding motion of the wand assembly to disinfect the surface of the component.

Figure 12:
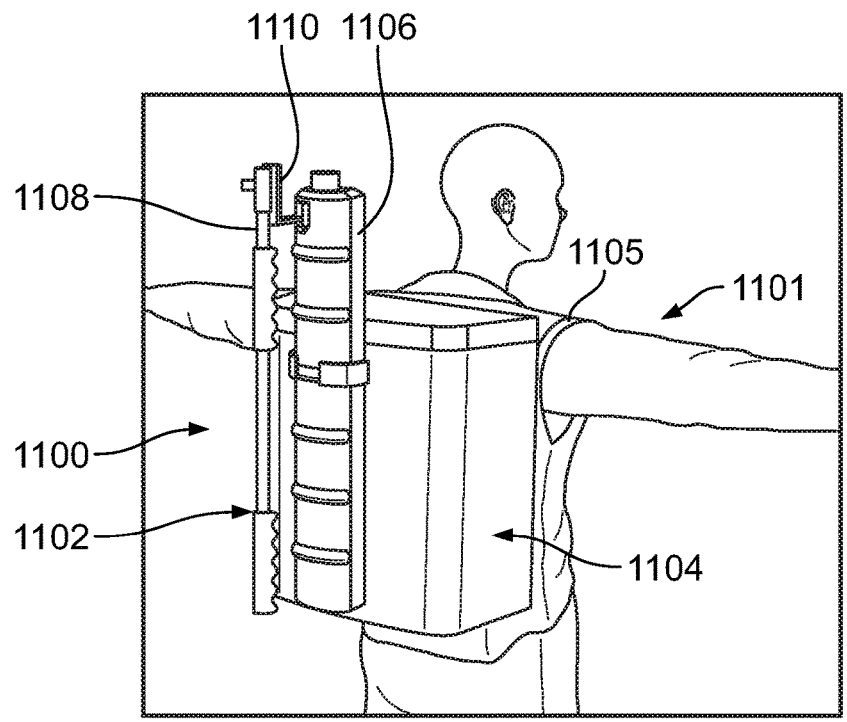
FIG. 12 illustrates a perspective view of a portable sanitizing system worn by an individual, according to an embodiment of the present disclosure.

FIG. 12 illustrates a perspective view of a portable sanitizing system 1100 worn by an individual 1101, according to an embodiment of the present disclosure. The portable sanitizing system 1100 includes a wand assembly 1102 coupled to a backpack assembly 1104 that is removably secured to the individual through a harness 1105. The wand assembly 1102 includes a sanitizing head 1106 coupled to a handle 1108. In at least one embodiment, the sanitizing head 1106 is moveably coupled to the handle 1108 through a coupler 1110.

The wand assembly 1102 is an example of the wand assembly 102 shown and described with respect to FIG. 1, for example. In at least one embodiment, the wand assembly 1102 includes range light sources and is configured to guide pacing motion and timing through visual cues from ranging light output by the range light sources.

As shown in FIG. 12, the wand assembly 1102 is in a stowed position. In the stowed position, the wand assembly 1102 is removably secured to a portion of the backpack assembly 1104, such as through one or more tracks, clips, latches, belts, ties, and/or the like.

Figure 13:
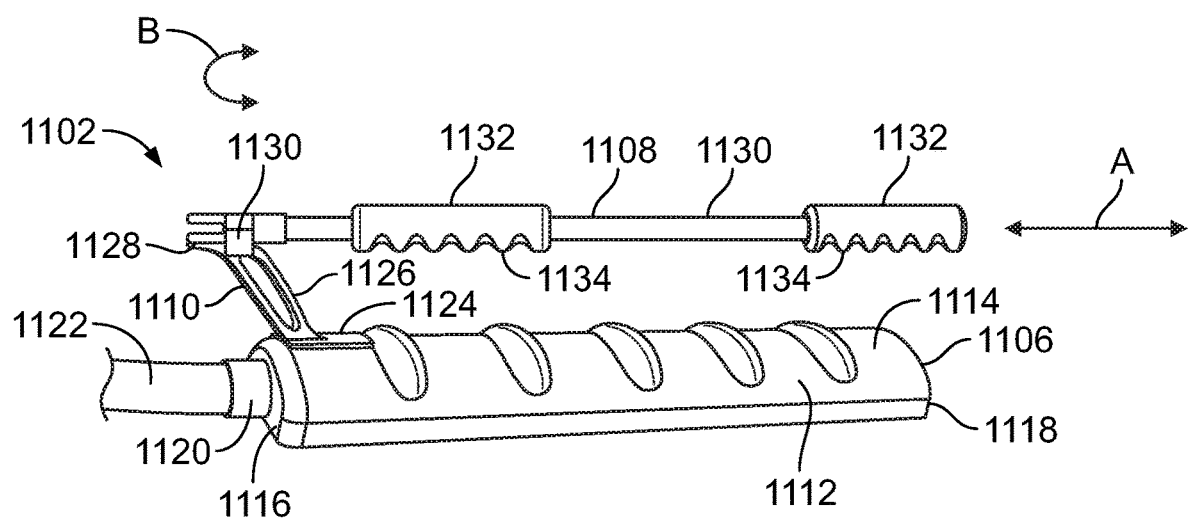
FIG. 13 illustrates a perspective lateral top view of a wand assembly, according to an embodiment of the present disclosure.

FIG. 13 illustrates a perspective lateral top view of the wand assembly 1102, according to an embodiment of the present disclosure. The sanitizing head 1106 couples to the handle 1108 through the coupler 1110. The sanitizing head 1106 includes a shroud 1112 having an outer cover 1114 that extends from a proximal end 1116 to a distal end 1118. As described herein, the shroud 1112 contains a UV lamp.

A port 1120 extends from the proximal end 1116. The port 1120 couples to a hose 1122, which, in turn, couples to the backpack assembly 1104 (shown in FIG. 12). The hose 1122 contains electrical cords, cables, wiring, or the like that couples a power source or supply (such as one or more batteries) within the backpack assembly 1104 (shown in FIG. 1) to a UV lamp 1140 within the shroud 1112. Optionally, the electrical cords, cables, wiring, or the like may be outside of the hose 1122. The hose 1122 also contains an air delivery line, such as an air tube) that fluidly couples an internal chamber of the shroud 1112 to an air blower, vacuum generator, air filters, and/or the like within the backpack assembly 1104.

The coupler 1110 is secured to the outer cover 1114 of the shroud 1112, such as proximate to the proximal end 1116. The coupler 1110 may include a securing beam 1124 secured to the outer cover 1114, such as through one or more fasteners, adhesives, and/or the like. An extension beam 1126 outwardly extends from the securing beam 1124, thereby spacing the handle 1108 from the shroud 1112. A bearing assembly 1128 extends from the extension beam 1126 opposite from the securing beam 1124. The bearing assembly 1128 includes one or more bearings, tracks, and/or the like, which allow the handle 1108 to linearly translate relative to the coupler 1110 in the directions of arrows A, and/or pivot about a pivot axle in the directions of arc B. Optionally, the securing beam 1124 may include a bearing assembly that allows the sanitizing head 1106 to translate in the directions of arrows A, and/or rotate (for example, swivel) in the directions of arc B in addition to, or in place of, the handle 1108 being coupled to the bearing assembly 1128 (for example, the handle 1108 may be fixed to the coupler 1110).

In at least one embodiment, the handle 1108 includes a rod, pole, beam, or the like 1130, which may be longer than the shroud 1112. Optionally, the rod 1130 may be shorter than the shroud 1112. One or more grips 1132 are secured to the rod 1130. The grips 1132 are configured to be grasped and held by an individual. The grips 1132 may include ergonomic tactile features 1134.

Optionally, the wand assembly 1102 may be sized and shaped differently than shown. For example, in at least one embodiment, the handle 1108 may be fixed in relation to the shroud 1112. Further, the handle 1108 may or may not be configured to move relative to itself and/or the shroud 1112. For example, the handle 1108 and the shroud 1112 may be integrally molded and formed as a single unit.

In at least one embodiment, the wand assembly 1102 is not coupled to a backpack assembly. For example, the wand assembly 1102 is a standalone unit having a power source, such as one or more batteries. As another example, the wand assembly 1102 is coupled to a case assembly. In at least one other embodiment, the wand assembly 1102 is coupled to a UV light sanitizing cart.

Figure 14:
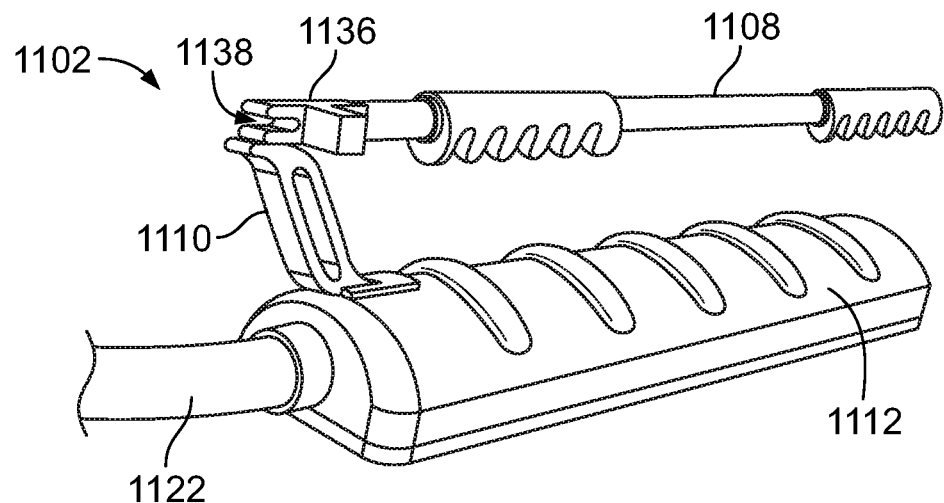
FIG. 14 illustrates a perspective rear view of the wand assembly of FIG. 2.
Figure 15:
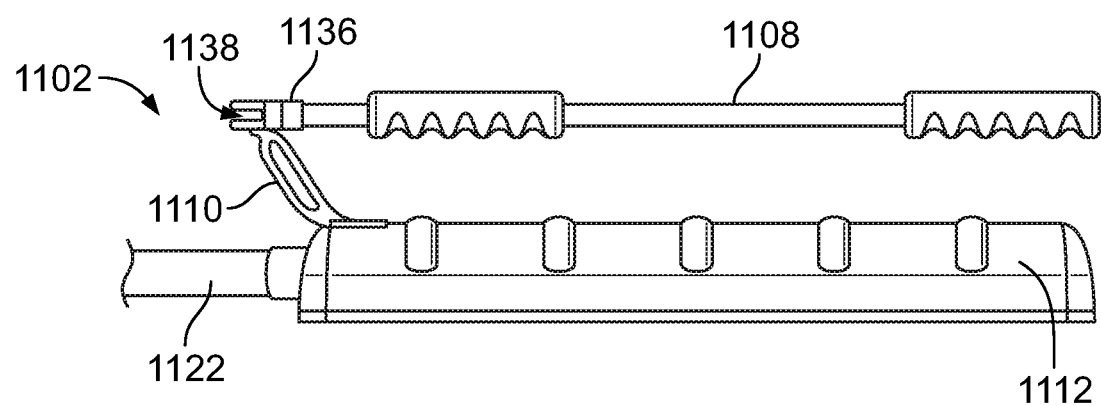
FIG. 15 illustrates a perspective lateral view of the wand assembly of FIG. 2.

FIG. 14 illustrates a perspective rear view of the wand assembly 1102 of FIG. 13. FIG. 15 illustrates a perspective lateral view of the wand assembly 1102 of FIG. 13. Referring to FIGS. 14 and 15, the handle 1108 may pivotally couple to the coupler 1110 through a bearing 1136 having a pivot axle 1138 that pivotally couples the handle 1108 to the coupler 1110. The handle 1108 may further be configured to linearly translate into and out of the bearing 1136. For example, the handle 1108 may be configured to telescope in and out. Optionally, or alternatively, in at least one embodiment, the handle 1108 may include a telescoping body that allows the handle 1108 to outwardly extend and inwardly recede.

Figure 16:
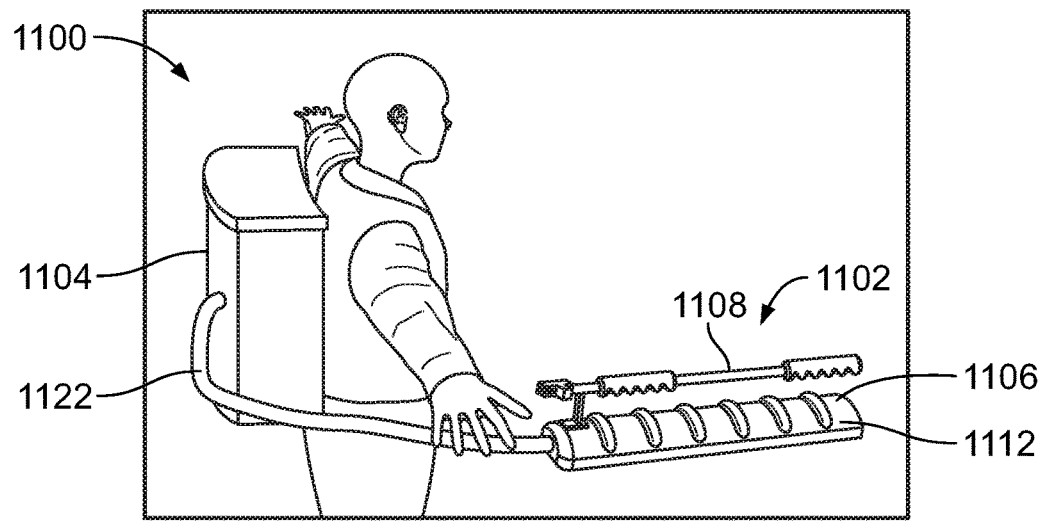
FIG. 16 illustrates a perspective view of the portable sanitizing system in a compact deployed position, according to an embodiment of the present disclosure.

FIG. 16 illustrates a perspective view of the portable sanitizing system 1100 in a compact deployed position, according to an embodiment of the present disclosure. The wand assembly 1102 is removed from the backpack assembly 1104 (as shown in FIG. 12) into the compact deployed position, as shown in FIG. 16. The hose 1122 connects the wand assembly 1102 to the backpack assembly 1104. In the compact deployed position, the sanitizing head 1106 is fully retracted in relation to the handle 1108.

Figure 17:
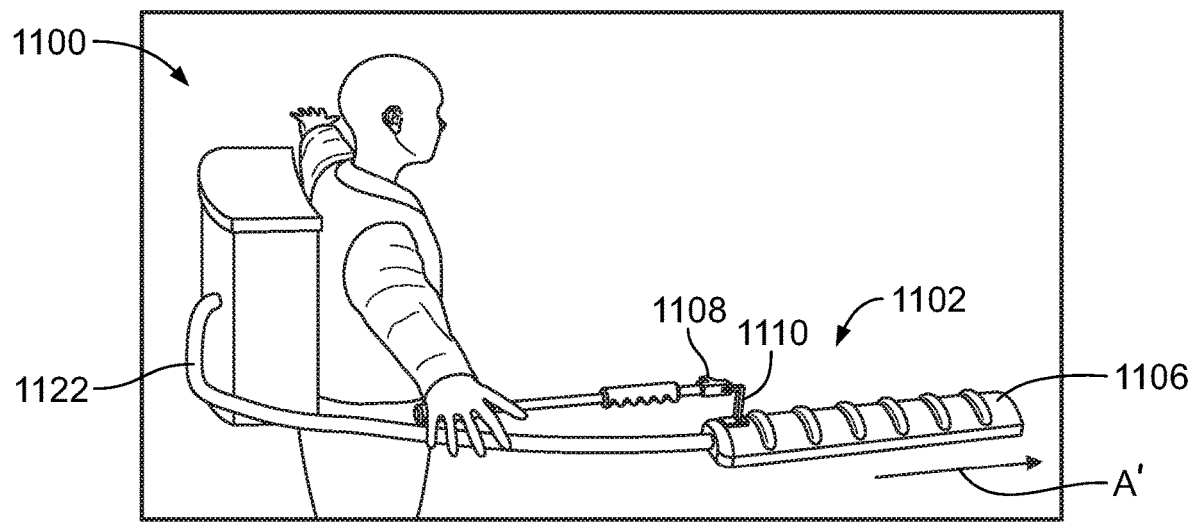
FIG. 17 illustrates a perspective view of the portable sanitizing system having a sanitizing head in an extended position, according to an embodiment of the present disclosure.

FIG. 17 illustrates a perspective view of the portable sanitizing system 1100 having the sanitizing head 1106 in an extended position, according to an embodiment of the present disclosure. In order to extend the sanitizing head 1106 relative to the handle 1108, the sanitizing head 1106 is outwardly slid relative to the handle 1108 in the direction of arrow A' (or the handle 1108 is rearwardly slid relative to the sanitizing head 1106). As noted, the sanitizing head 1106 is able to linearly translate in the direction of arrow A' relative to the handle 1108 via the coupler 1110. The outward extension of the sanitizing head 1106, as shown in FIG. 17, allows for the portable sanitizing system 1100 to easily reach distant areas. Alternatively, the sanitizing head 1106 may not linearly translate relative to the handle 1108.

Figure 18:
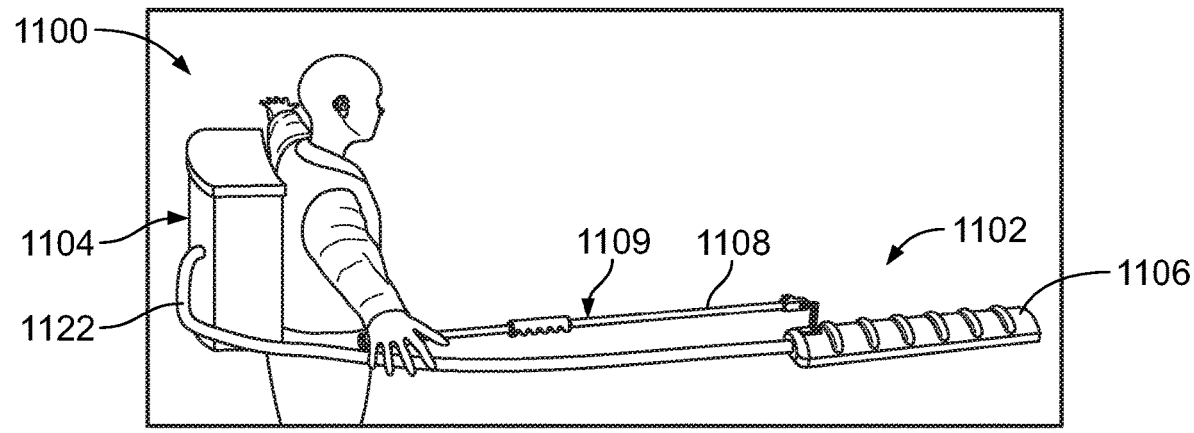
FIG. 18 illustrates a perspective view of the portable sanitizing system having the sanitizing head in an extended position and a handle in an extended position, according to an embodiment of the present disclosure.

FIG. 18 illustrates a perspective view of the portable sanitizing system 1100 having the sanitizing head 1106 in an extended position and the handle 1108 in an extended position, according to an embodiment of the present disclosure. To reach even further, the handle 1108 may be configured to linearly translate, such as through a telescoping portion, to allow the sanitizing head 1106 to reach further outwardly. Alternatively, the handle 1108 may not be configured to extend and retract.

In at least one embodiment, the handle 1108 may include a lock 1109. The lock 1109 is configured to be selectively operated to secure the handle 1108 into a desired extended (or retracted) position.

Figure 19:
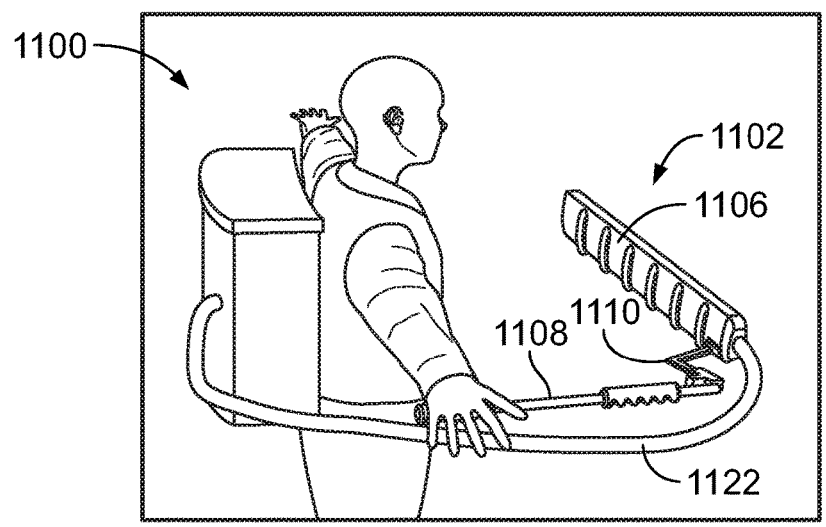
FIG. 19 illustrates a perspective view of the portable sanitizing system having the sanitizing head rotated in relation to the handle, according to an embodiment of the present disclosure.

FIG. 19 illustrates a perspective view of the portable sanitizing system 1100 having the sanitizing head 1106 rotated in relation to the handle 1108, according to an embodiment of the present disclosure. As noted, the sanitizing head 1106 is configured to rotate relative to the handle 1108 via the coupler 1110. Rotating the sanitizing head 1106 relative to the handle 1108 allows the sanitizing head 1106 to be moved to a desired position, and sweep or otherwise reach into areas that would otherwise be difficult to reach if the sanitizing head 1106 was rigidly fixed to the handle 1108. Alternatively, the sanitizing head 1106 may not be rotatable relative to the handle 1108.

Figure 20:
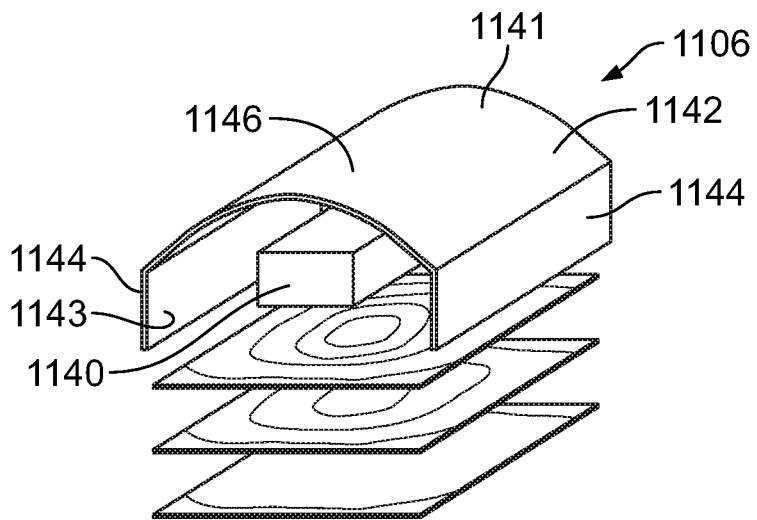
FIG. 20 illustrates a perspective end view of a UV lamp and a reflector of the sanitizing head, according to an embodiment of the present disclosure.

FIG. 20 illustrates a perspective end view of a UV lamp 1140 and a reflector 1142 of the sanitizing head 1106, according to an embodiment of the present disclosure. The UV lamp 1140 and the reflector 1142 are secured within the shroud 1112 (shown in FIG. 13, for example) of the sanitizing head 1106. In at least one embodiment, the reflector 1142 is secured to an underside 1141 of the shroud 1112, such as through one or more adhesives. As another example, the reflector 1142 is an integral part of the shroud 1112. For example, the reflector 1142 may be or otherwise provide the underside 1141 of the shroud 1112. The reflector 1142 provides a reflective surface 1143 (such as formed of Teflon, a mirrored surface, and/or the like) that is configured to outwardly reflect UV light emitted by the UV lamp 1140. In at least one example, shroud 1112 may be or include a shell formed of fiberglass, and the reflector 1142 may be formed of Teflon that provides a 98% reflectivity.

The reflector 1142 may extend along an entire length of the underside 1141 of the shroud 1112. Optionally, the reflector 1142 may extend along less than an entire length of the underside 1141 of the shroud 1112.

The UV lamp 1140 may extend along an entire length (or along substantially the entire length, such as between the ends 1116 and 1118). The UV lamp 1140 is secured to the reflector 1142 and/or the shroud 1112 through one or more brackets, for example. The UV lamp 1140 includes one or more UV light emitters, such as one more bulbs, light emitting elements (such as light emitting diodes), and/or the like. In at least one embodiment, the UV lamp 1140 is configured to emit UV light in the far UV spectrum, such as at a wavelength between 200 nm-230 nm. In at least one embodiment, the UV lamp 1140 is configured to emit UV light having a wavelength of 222 nm. For example, the UV lamp 1140 may be or include a 300 W bulb that is configured to emit UV light having a wavelength of 222 nm. Optionally, the UV lamp 1140 may emit UV light having a different wavelength, such as within the UVC spectrum.

In at least one other embodiment, the UV lamp 1140 is configured to emit UV light in the UVC spectrum, such as at a wavelength between 230 nm-280 nm. In at least one embodiment, the UV lamp 1140 is configured to emit UV light having a wavelength of 254 nm.

As shown, the reflector 1142 includes flat, upright side walls 1144 connected together through an upper curved wall 1146. The upper curved wall 1146 may be bowed outwardly away from the UV lamp 1140. For example, the upper curved wall 1146 may have a parabolic cross-section and/or profile.

It has been found that the straight, linear side walls 1144 provide desired reflection and/or focusing of UV light emitted from the UV lamp 1140 toward and onto a desired location. Alternatively, the side walls 1144 may not be linear and flat.

Figure 21:
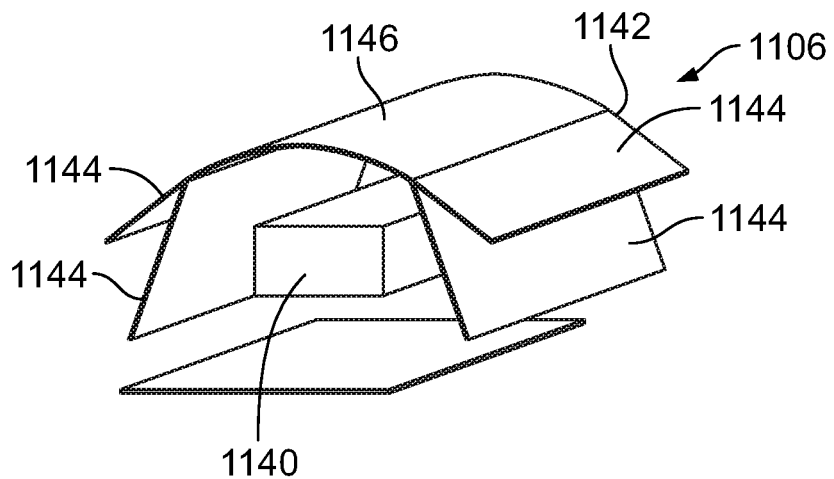
FIG. 21 illustrates a perspective end view of a UV lamp and a reflector of the sanitizing head, according to an embodiment of the present disclosure.

FIG. 21 illustrates a perspective end view of the UV lamp 1140 and a reflector 1142 of the sanitizing head 1106, according to an embodiment of the present disclosure. The reflector 1142 shown in FIG. 21 is similar to the reflector 1142 shown in FIG. 20, except that the side walls 1144 may outwardly cant from the upper curved wall 1146.

Figure 22:
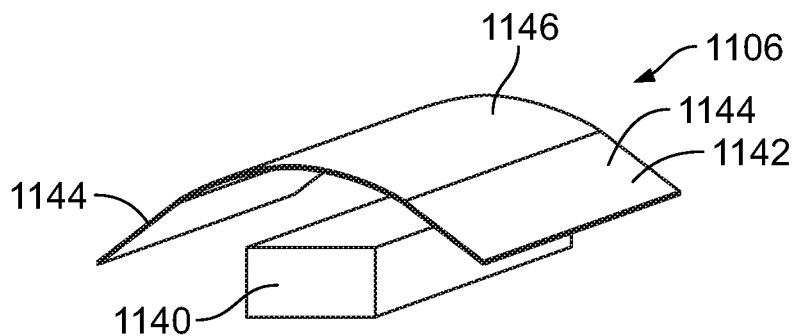
FIG. 22 illustrates a perspective end view of a UV lamp and a reflector of the sanitizing head, according to an embodiment of the present disclosure.

FIG. 22 illustrates a perspective end view of the UV lamp 1140 and the reflector 1142 of the sanitizing head, according to an embodiment of the present disclosure. In this embodiment, the side walls 1144 may be curved according to the curvature of the upper curved wall 1146.

Figure 23:
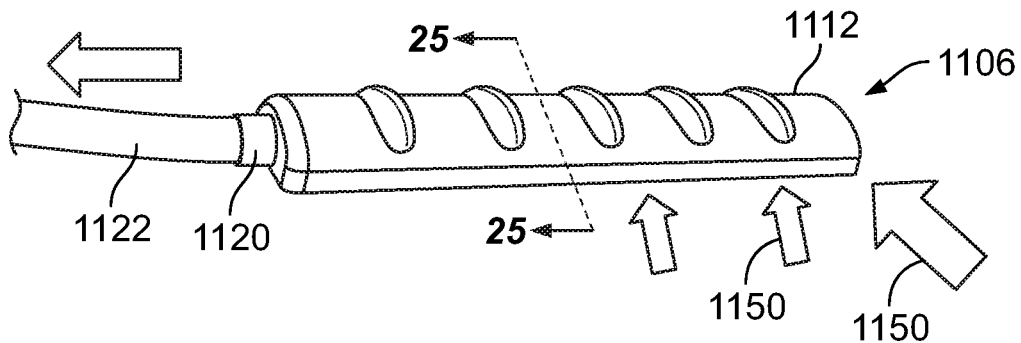
FIG. 23 illustrates a perspective top view of the sanitizing head.
Figure 24:
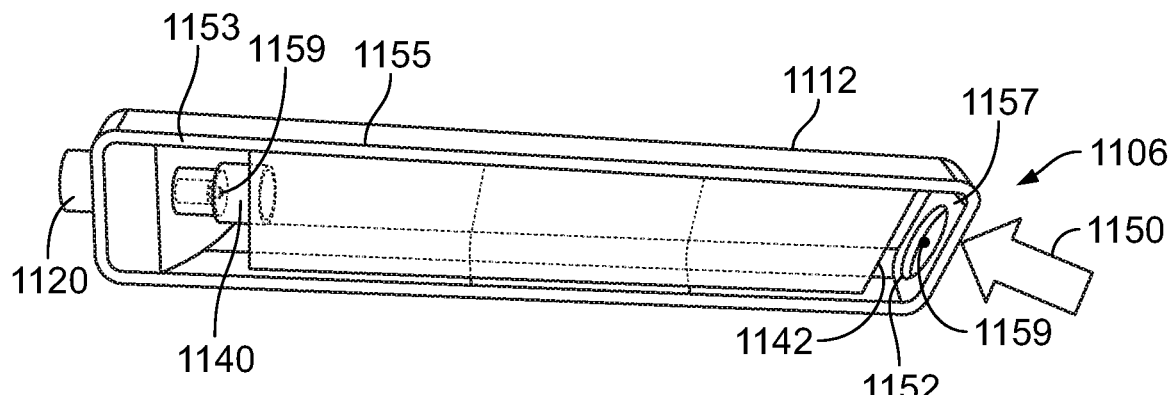
FIG. 24 illustrates a perspective bottom view of the sanitizing head.
Figure 25:
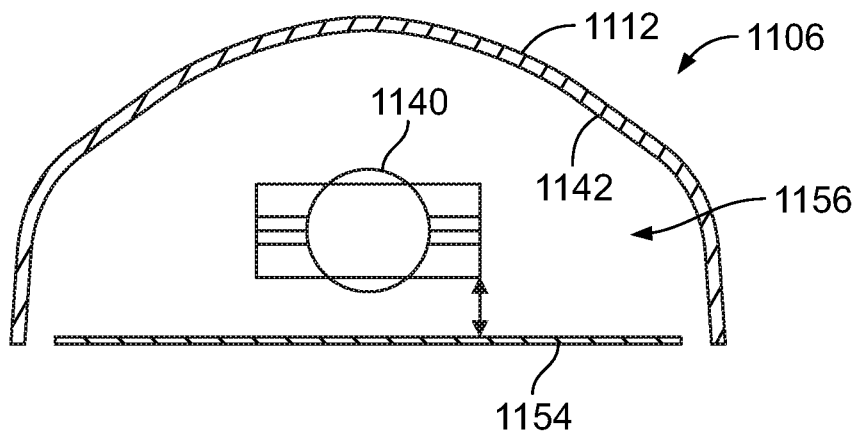
FIG. 25 illustrates an axial cross-sectional view of the sanitizing head through line 25-25 of FIG. 23.

FIG. 23 illustrates a perspective top view of the sanitizing head 1106. FIG. 24 illustrates a perspective bottom view of the sanitizing head 1106. FIG. 25 illustrates an axial cross-sectional view of the sanitizing head 1106 through line 25-25 of FIG. 23. Referring to FIGS. 23-25, air 1150 is configured to be drawn into the sanitizing head 1106 through one or more openings 1152 (or simply an open chamber) of the shroud 1112. The air 1150 is drawn into the sanitizing head 1106, such as via a vacuum generator within the backpack assembly 1104 (shown in FIG. 12). The air 1150 is drawn into the shroud 1112, and cools the UV lamp 1140 as it passes over and around the UV lamp 1140. The air 1150 passes into the port 1120 and into the hose 1122, such as within an air tube within the hose 1122. The air 1150 not only cools the UV lamp 1140, but also removes ozone, which may be generated by operation of the UV lamp 1140, within the shroud 1112. The air 1150 may be drawn to an air filter, such as an activated carbon filter, within the backpack assembly 1104.

In at least one embodiment, the portable sanitizing system 1100 may also include an alternative ozone mitigation system. As an example, the ozone mitigation system may be disposed in the shroud 1112 or another portion of the system, and may include an inert gas bath, or a face inert gas system, such as in U.S. Pat. No. 10,232,954.

Referring to FIG. 23, in particular, a bumper 1153 may be secured to an exposed lower circumferential edge 1155 of the shroud 1112. The bumper 1153 may be formed of a resilient material, such as rubber, another elastomeric material, open or closed cell foam, and/or the like. The bumper 1153 protects the sanitizing head 1106 from damage in case the sanitizing head 1106 inadvertently contacts a surface. The bumper 1153 also protects the surface from damage.

The openings 1152 may be spaced around the lower surface of the shroud 1112 such that they do not provide a direct view of the UV lamp 1140. For example, the openings 1152 may be positioned underneath portions that are spaced apart from the UV lamp 1140.

Referring to FIG. 25, in particular, the sanitizing head 1106 may include a cover plate 1154 below the UV lamp 1140. The cover plate 1154 may be formed of glass, for example, and may be configured to filter UV light emitted by the UV lamp 1140. The UV lamp 1140 may be secured within an interior chamber 1156 defined between the reflector 1142 and the cover plate 1154. In at least one embodiment, the cover plate 1154 is or otherwise includes a far UV band pass filter. For example, the cover plate 1154 may be a 222 nm band pass filter that filters UV light emitted by the UV lamp 1140 to a 222 nm wavelength. As such, UV light that is emitted from the sanitizing head 1106 may be emitted at a wavelength of 222 nm.

Referring to FIGS. 24 and 25, a rim 1157 (such as a 0.020" thick Titanium rim) may connect the cover plate 1154 to the shroud 1112. The rim 1157 may distribute impact loads therethrough and/or therearound.

In at least one embodiment, ranging light emitting diodes (LEDs) 1159 (which are examples of the range light sources) may be disposed proximate to ends of the UV lamp 1140. The ranging LEDs 1159 may be used to determine a desired range to a structure that is to be sanitized, for example. In at least one embodiment, the ranging LEDs 1159 may be disposed on or within the rim 1157 and/or the cover plate 1154.

Figure 26:
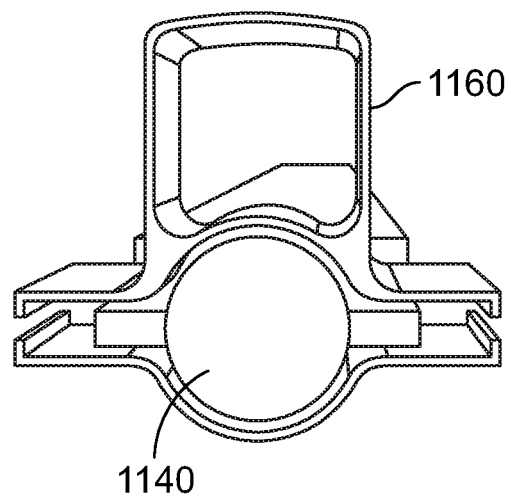
FIG. 26 illustrates a perspective end view of the UV lamp secured to a mounting bracket, according to an embodiment of the present disclosure.

FIG. 26 illustrates a perspective end view of the UV lamp 1140 secured to a mounting bracket or clamp 1160, according to an embodiment of the present disclosure. Each end of the UV lamp 1140 may be coupled to a mounting bracket or clamp 1160, which secures the UV lamp 1140 to the shroud 1112 (shown in FIGS. 23-25). A buffer, such as a thin (for example, 0.040") sheet of silicon may be disposed between the end of the UV lamp 1140 and the bracket 1160. Optionally, the UV lamp 1140 may be secured to the shroud 1112 through brackets or clamps that differ in size and shape than shown. As another example, the UV lamp 1140 may be secured to the shroud 1112 through adhesives, fasteners, and/or the like.

Figure 27:
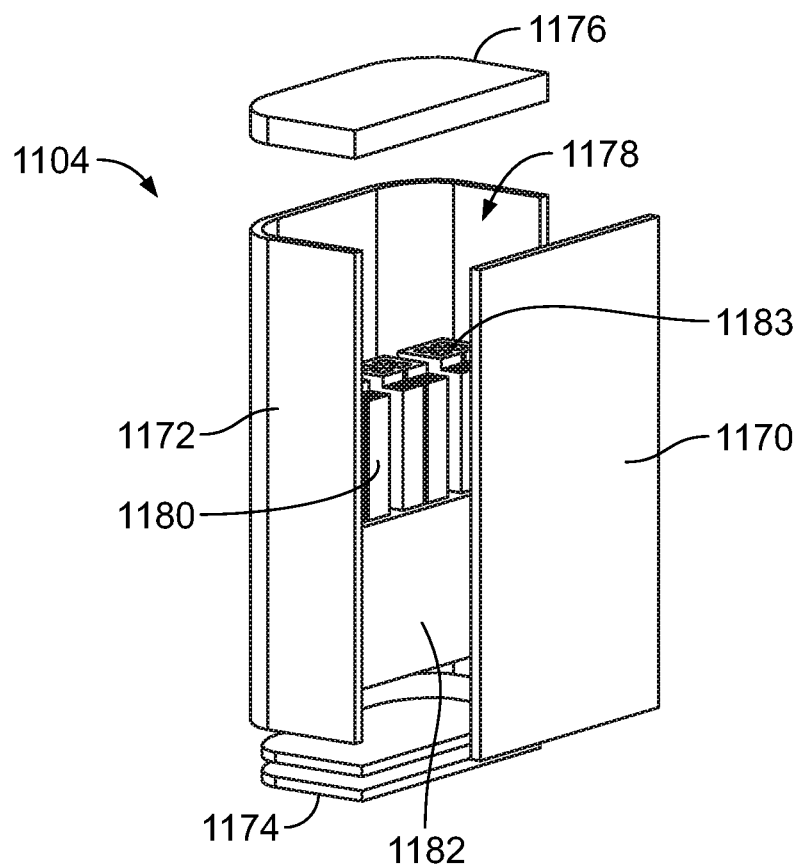
FIG. 27 illustrates a perspective exploded view of a backpack assembly, according to an embodiment of the present disclosure.

FIG. 27 illustrates a perspective exploded view of the backpack assembly 1104, according to an embodiment of the present disclosure. The backpack assembly 1104 includes a front wall 1170 that couples to a rear shell 1172, a base 1174, and a top cap 1176. An internal chamber 1178 is defined between the front wall 1170, the rear shell 1172, the base 1174, and the top cap 1176. One or more batteries 1180, such as rechargeable Lithium batteries, are contained within the internal chamber 1178. An air generation sub-system 1182 is also contained within the internal chamber 1178. The air generation sub-system 1182 is in fluid communication with an air tube within the hose 1122 (shown in FIG. 14, for example). The air generation sub-system 1182 may include an airflow device, such as a vacuum generator, an air blower, and/or the like. The airflow device is configured to generate airflow to cool the UV lamp, draw air from the sanitizing head 1106 into the backpack assembly 1104 and out through an exhaust, draw or otherwise remove generated ozone away from the shroud 1112, and/or the like.

One or more air filters 1183, such as carbon filters, are within the backpack assembly 1104. The air filters 1183 are in communication with the air tube or other such delivery duct or line that routes air through the hose 1122 and into the backpack assembly 1104. The air filters 1183 are configured to filter the air that is drawn into the backpack assembly 1104 from the shroud 1112. For example, the air filters 1183 may be configured to remove, deactivate, or otherwise neutralize ozone.

The batteries 1180 and/or a power supply within the backpack assembly 1104 provides operating power for the UV lamp 1140 of the sanitizing head 1106 (shown in FIG. 14, for example). The top wall 1176 may be removably coupled to the front wall 1170 and the rear shell 1172. The top wall 1176 may be removed to provide access to the batteries 1180 (such as to remove and/or recharge the batteries), for example. Additional space may be provided within the backpack assembly 1104 for storage of supplies, additional batteries, additional components, and/or the like. In at least one embodiment, the front wall 1170, the rear shell 1172, the base 1174, and the top cap 1176 may be formed of fiberglass epoxy.

Figure 28:
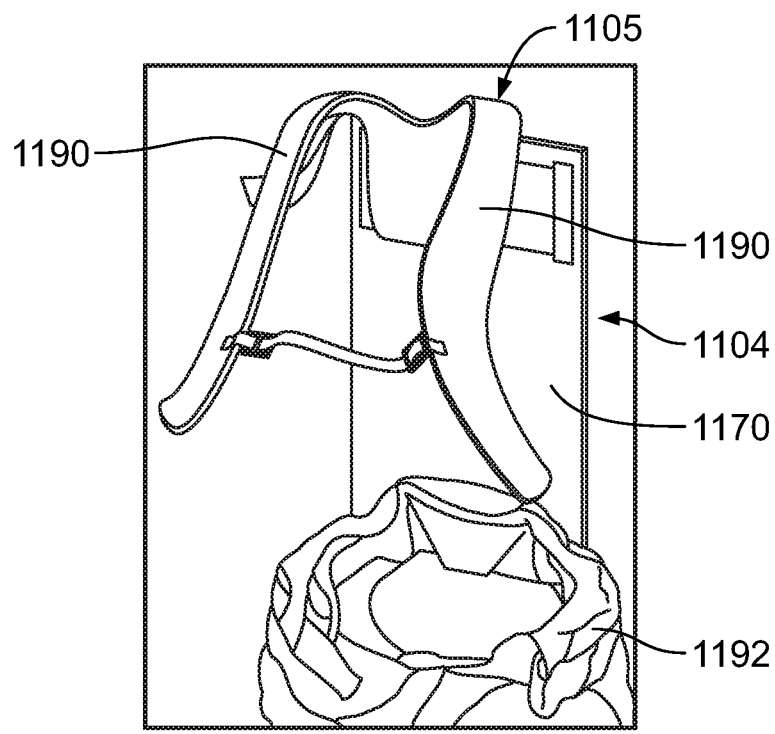
FIG. 28 illustrates a perspective front view of a harness coupled to a backpack assembly, according to an embodiment of the present disclosure.

FIG. 28 illustrates a perspective front view of the harness 1105 coupled to the backpack assembly 1104, according to an embodiment of the present disclosure. The harness 1105 may include shoulder straps 1190 and/or a waist or hip belt or strap 1192, which allow the individual to comfortably wear the backpack assembly 1104.

Referring to FIGS. 12-28, in operation, the individual may walk through an area wearing the backpack assembly 1104. When a structure to be sanitized is found, the individual may position grasp the handle 1108 and position the sanitizing head 1106 as desired, such as by extending and/or rotating the sanitizing head 1106 relative to the handle 1108. The individual may then engage an activation button on the handle 1108, for example, to activate the UV lamp 1140 to emit sanitizing UV light onto the structure. As the UV lamp 1140 is activated, air 1150 is drawn into the shroud 1112 to cool the UV lamp 1140, and divert any generated ozone into the backpack assembly 1104, where it is filtered by the air filters 1183.

The extendable wand assembly 1102 allows the sanitizing head 1106 to reach distant areas, such as over an entire set of three passenger seats, from a row within an internal cabin of a commercial aircraft.

Figure 29:
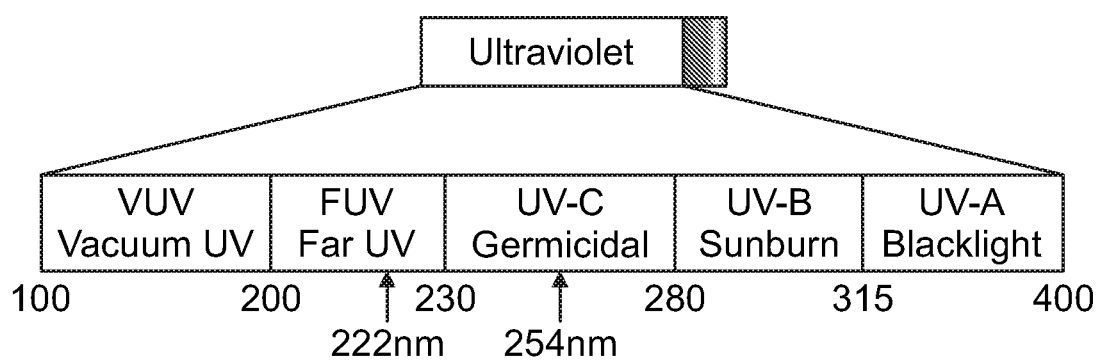
FIG. 29 illustrates an ultraviolet light spectrum.

FIG. 29 illustrates an ultraviolet light spectrum. Referring to FIGS. 12-29, in at least one embodiment, the sanitizing head 1106 is configured to emit sanitizing UV light (through operation of the UV lamp 1140) within a far UV spectrum, such as between 200 nm to 230 nm. In at least one embodiment, the sanitizing head 1106 emits sanitizing UV light having a wavelength of 222 nm.

In at least one other embodiment, the sanitizing head 1106 is configured to emit sanitizing UV light within the UVC spectrum, such as between 230 nm-280 nm. In at least one embodiment, the sanitizing head 1106 emits sanitizing UV light having a wavelength of 254 nm.

Figure 30:
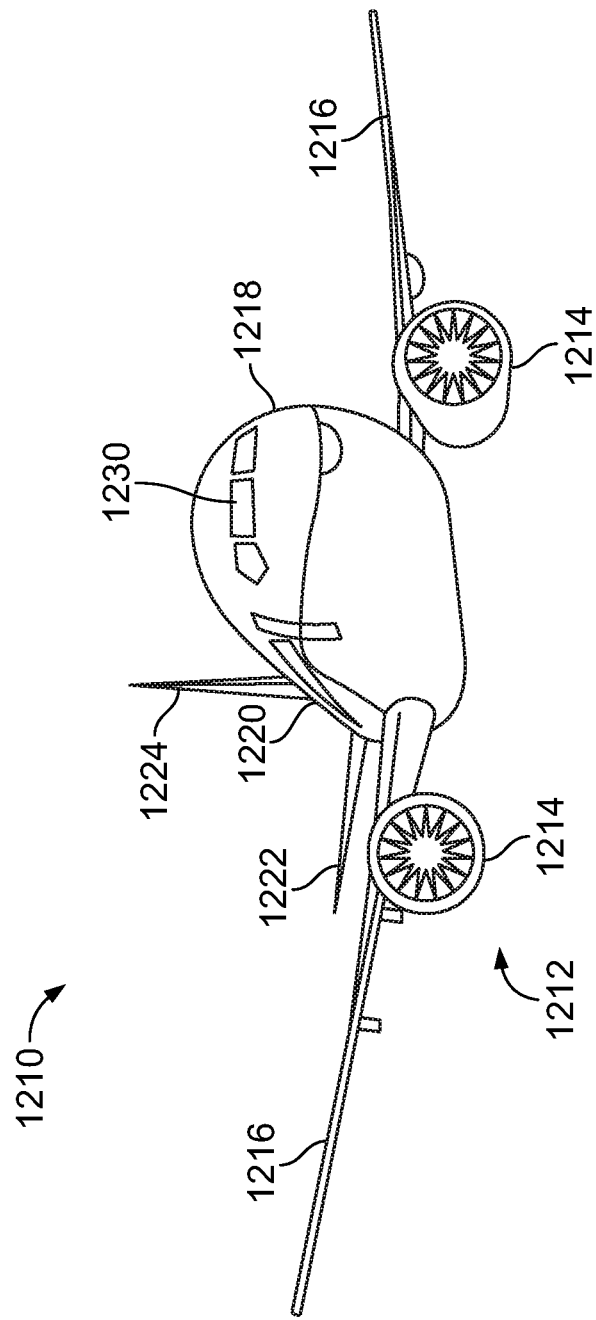
FIG. 30 illustrates a perspective front view of an aircraft, according to an embodiment of the present disclosure.

FIG. 30 illustrates a perspective front view of an aircraft 1210, according to an embodiment of the present disclosure. The aircraft 1210 includes a propulsion system 1212 that includes engines 1214, for example. Optionally, the propulsion system 1212 may include more engines 1214 than shown. The engines 1214 are carried by wings 1216 of the aircraft 1210. In other embodiments, the engines 1214 may be carried by a fuselage 1218 and/or an empennage 1220. The empennage 1220 may also support horizontal stabilizers 1222 and a vertical stabilizer 1224.

The fuselage 1218 of the aircraft 1210 defines an internal cabin 1230, which includes a flight deck or cockpit, one or more work sections (for example, galleys, personnel carry-on baggage areas, and the like), one or more passenger sections (for example, first class, business class, and coach sections), one or more lavatories, and/or the like. The internal cabin 1230 includes one or more lavatory systems, lavatory units, or lavatories, as described herein.

Embodiments of the present disclosure are used to disinfect various components within the internal cabin 1230. Alternatively, instead of an aircraft, embodiments of the present disclosure may be used with various other vehicles, such as automobiles, buses, locomotives and train cars, watercraft, and the like. Further, embodiments of the present disclosure may be used with respect to fixed structures, such as commercial and residential buildings.

Figure 31A:
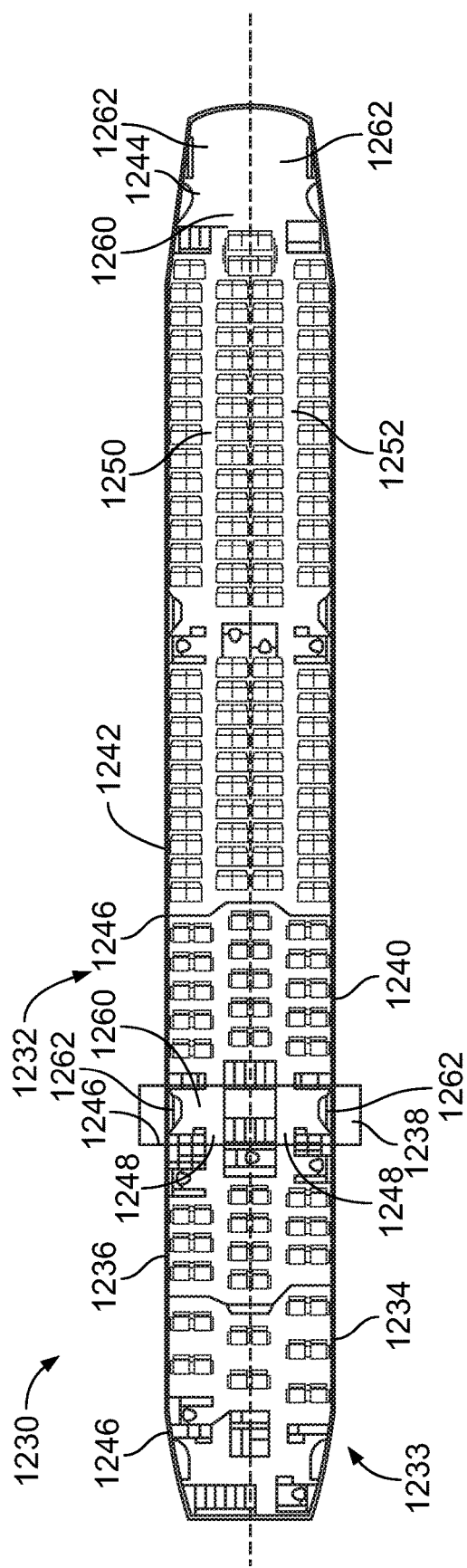
FIG. 31A illustrates a top plan view of an internal cabin of an aircraft, according to an embodiment of the present disclosure.

FIG. 31A illustrates a top plan view of an internal cabin 1230 of an aircraft, according to an embodiment of the present disclosure. The internal cabin 1230 may be within the fuselage 1232 of the aircraft, such as the fuselage 1218 of FIG. 30. For example, one or more fuselage walls may define the internal cabin 1230. The internal cabin 1230 includes multiple sections, including a front section 1233, a first class section 1234, a business class section 1236, a front galley station 1238, an expanded economy or coach section 1240, a standard economy of coach section 1242, and an aft section 1244, which may include multiple lavatories and galley stations. It is to be understood that the internal cabin 1230 may include more or less sections than shown. For example, the internal cabin 1230 may not include a first class section, and may include more or less galley stations than shown. Each of the sections may be separated by a cabin transition area 1246, which may include class divider assemblies between aisles 1248.

As shown in FIG. 31A, the internal cabin 1230 includes two aisles 1250 and 1252 that lead to the aft section 1244. Optionally, the internal cabin 1230 may have less or more aisles than shown. For example, the internal cabin 1230 may include a single aisle that extends through the center of the internal cabin 1230 that leads to the aft section 1244.

The aisles 1248, 1250, and 1252 extend to egress paths or door passageways 1260. Exit doors 1262 are located at ends of the egress paths 1260. The egress paths 1260 may be perpendicular to the aisles 1248, 1250, and 1252. The internal cabin 1230 may include more egress paths 1260 at different locations than shown. The portable sanitizing system 1100 shown and described with respect to FIGS. 12-29 may be used to sanitize various structures within the internal cabin 1230, such as passenger seats, monuments, stowage bin assemblies, components on and within lavatories, galley equipment and components, and/or the like.

Figure 31B:
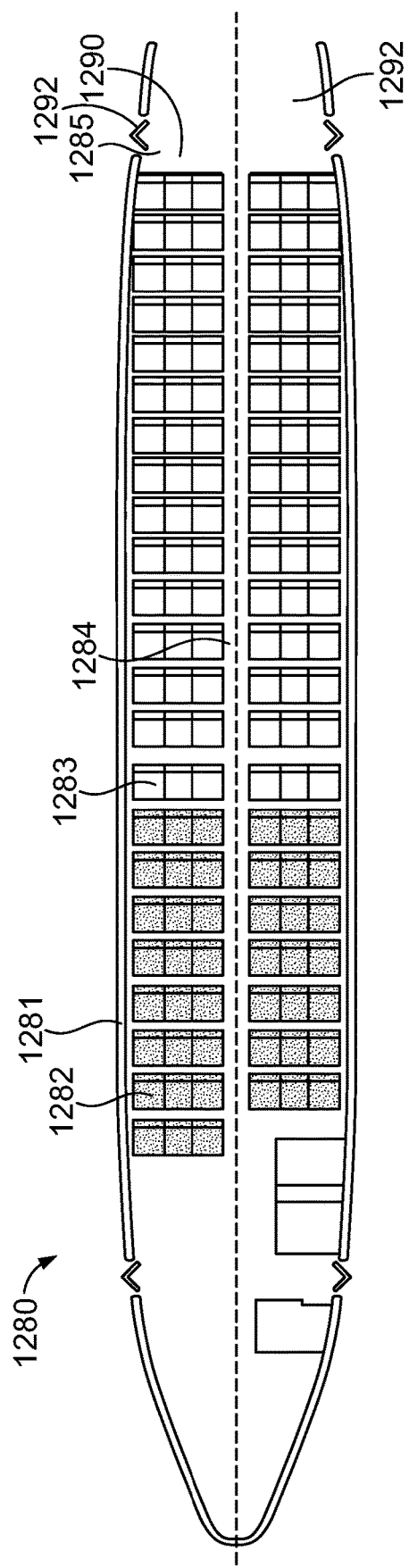
FIG. 31B illustrates a top plan view of an internal cabin of an aircraft, according to an embodiment of the present disclosure.

FIG. 31B illustrates a top plan view of an internal cabin 1280 of an aircraft, according to an embodiment of the present disclosure. The internal cabin 1280 is an example of the internal cabin 1230 shown in FIG. 30. The internal cabin 1280 may be within a fuselage 1281 of the aircraft. For example, one or more fuselage walls may define the internal cabin 1280. The internal cabin 1280 includes multiple sections, including a main cabin 1282 having passenger seats 1283, and an aft section 1285 behind the main cabin 1282. It is to be understood that the internal cabin 1280 may include more or less sections than shown.

The internal cabin 1280 may include a single aisle 1284 that leads to the aft section 1285. The single aisle 1284 may extend through the center of the internal cabin 1280 that leads to the aft section 1285. For example, the single aisle 1284 may be coaxially aligned with a central longitudinal plane of the internal cabin 1280.

The aisle 1284 extends to an egress path or door passageway 1290. Exit doors 1292 are located at ends of the egress path 1290. The egress path 1290 may be perpendicular to the aisle 1284. The internal cabin 1280 may include more egress paths than shown. The portable sanitizing system 1100 shown and described with respect to FIGS. 12-29 may be used to sanitize various structures within the internal cabin 1230, such as passenger seats, monuments, stowage bin assemblies, components on and within lavatories, galley equipment and components, and/or the like.

Figure 32:
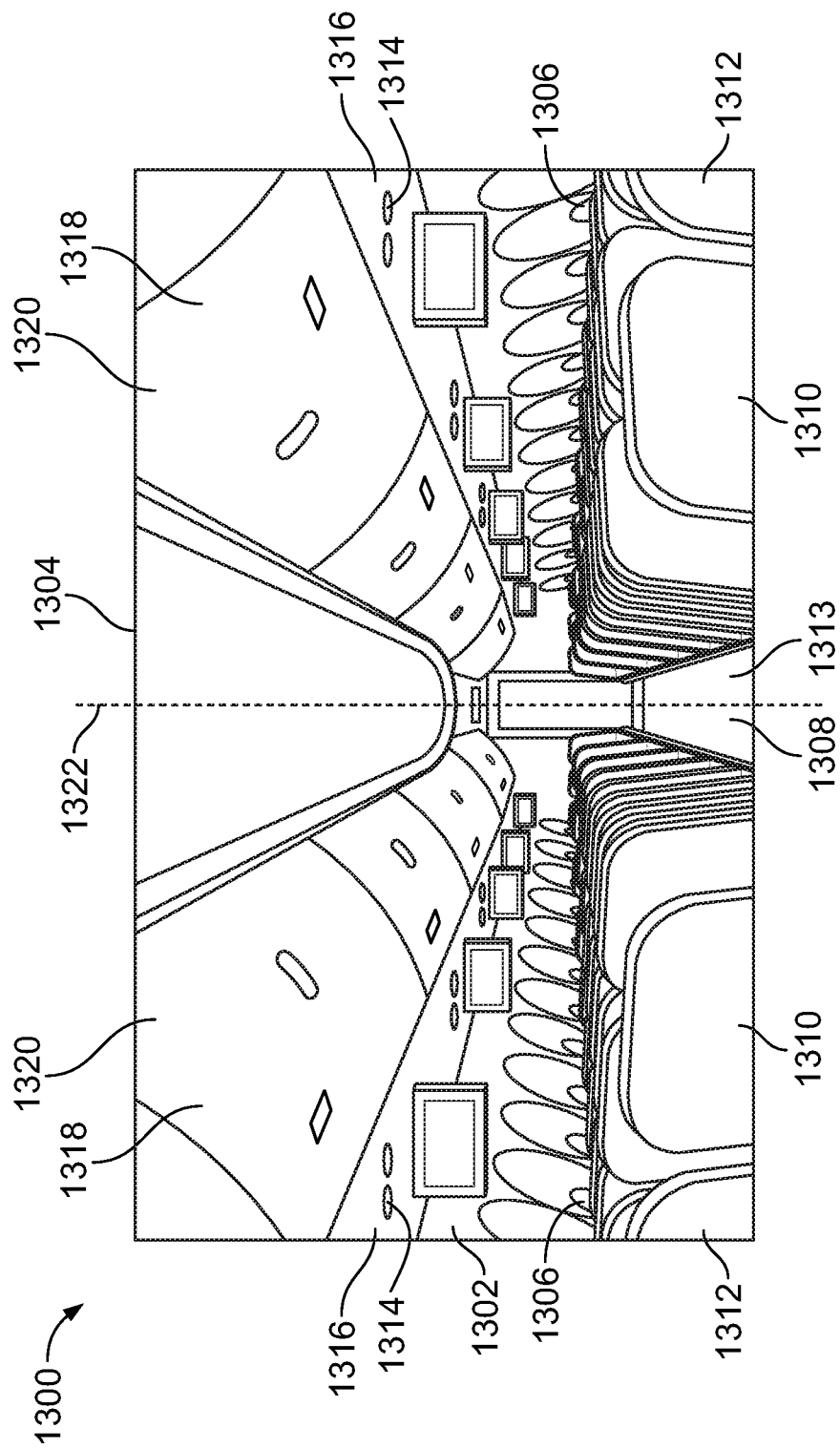
FIG. 32 illustrates a perspective interior view of an internal cabin of an aircraft, according to an embodiment of the present disclosure.

FIG. 32 illustrates a perspective interior view of an internal cabin 1300 of an aircraft, according to an embodiment of the present disclosure. The internal cabin 1300 includes outboard walls 1302 connected to a ceiling 1304. Windows 1306 may be formed within the outboard walls 1302. A floor 1308 supports rows of seats 1310. As shown in FIG. 32, a row 1312 may include two seats 1310 on either side of an aisle 1313. However, the row 1312 may include more or less seats 1310 than shown. Additionally, the internal cabin 1300 may include more aisles than shown.

Passenger service units (PSUs) 1314 are secured between an outboard wall 1302 and the ceiling 1304 on either side of the aisle 1313. The PSUs 1314 extend between a front end and rear end of the internal cabin 1300. For example, a PSU 1314 may be positioned over each seat 1310 within a row 1312. Each PSU 1314 may include a housing 1316 that generally contains vents, reading lights, an oxygen bag drop panel, an attendant request button, and other such controls over each seat 1310 (or groups of seats) within a row 1312.

Overhead stowage bin assemblies 1318 are secured to the ceiling 1304 and/or the outboard wall 1302 above and inboard from the PSU 1314 on either side of the aisle 1313. The overhead stowage bin assemblies 1318 are secured over the seats 1310. The overhead stowage bin assemblies 1318 extend between the front and rear end of the internal cabin 1300. Each stowage bin assembly 1318 may include a pivot bin or bucket 1320 pivotally secured to a strongback (hidden from view in FIG. 32). The overhead stowage bin assemblies 1318 may be positioned above and inboard from lower surfaces of the PSUs 1314. The overhead stowage bin assemblies 1318 are configured to be pivoted open in order to receive passenger carry-on baggage and personal items, for example.

As used herein, the term "outboard" means a position that is further away from a central longitudinal plane 1322 of the internal cabin 1300 as compared to another component. The term "inboard" means a position that is closer to the central longitudinal plane 1322 of the internal cabin 1300 as compared to another component. For example, a lower surface of a PSU 1314 may be outboard in relation to a stowage bin assembly 1318.

The portable sanitizing system 1100 shown and described with respect to FIGS. 12-29 may be used to sanitize various structures shown within the internal cabin 1300.

When not in use, the portable sanitizing system 1100 may be stored within a closet, galley cart bay, or galley cart, such as within the internal cabin of the vehicle.

Figure 33:
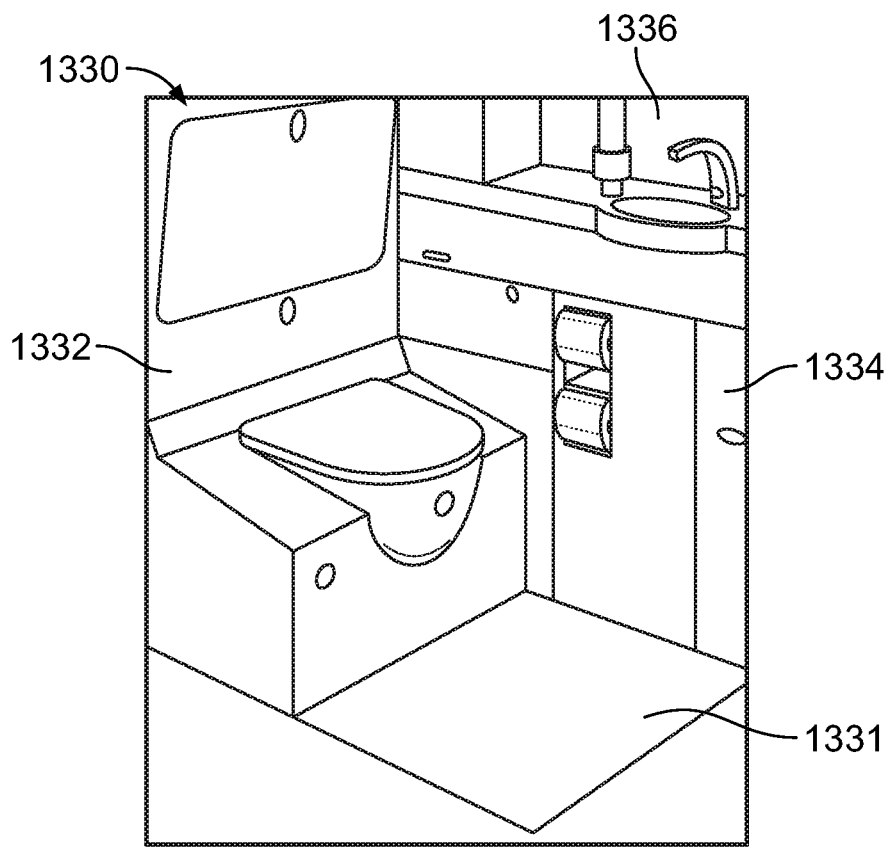
FIG. 33 illustrates a perspective internal view of a lavatory within an internal cabin of an aircraft.

FIG. 33 illustrates a perspective internal view of a lavatory 1330 within an internal cabin of a vehicle, such as any of the internal cabins described herein. The lavatory 1330 is an example of an enclosed space, monument or chamber, such as within the internal cabin a vehicle. The lavatory 1330 may be onboard an aircraft, as described above. Optionally, the lavatory 1330 may be onboard various other vehicles. In other embodiments, the lavatory 1330 may be within a fixed structure, such as a commercial or residential building. The lavatory 1330 includes a base floor 1331 that supports a toilet 1332, cabinets 1334, and a sink 1336 or wash basin. The lavatory 1330 may be arranged differently than shown. The lavatory 1330 may include more or less components than shown. The portable sanitizing system 1100 shown and described with respect to FIGS. 12-29 may be used to sanitize the various structures, components, and surfaces within the lavatory 1330.

Figure 34:
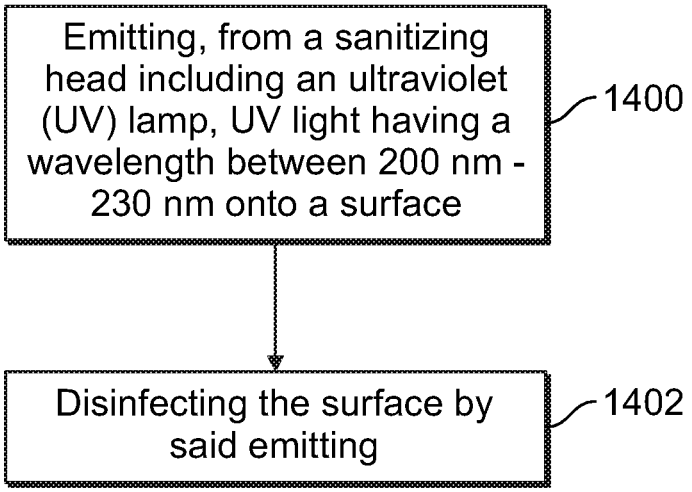
FIG. 34 illustrates a flow chart of a portable sanitizing method, according to an embodiment of the present disclosure.

FIG. 34 illustrates a flow chart of a portable sanitizing method, according to an embodiment of the present disclosure. The method includes emitting (1400), from a sanitizing head including an ultraviolet (UV) lamp, UV light having a wavelength between 200 nm-230 nm onto a surface; and disinfecting (1402) the surface by said emitting (1400). In at least one embodiment, said emitting (1400) includes emitting the UV light having a wavelength of 222 nm.

Optionally, the method include emitting UV light having a wavelength between 230 nm-280 nm. In at least one embodiment, said emitting include emitting the UV light having a wavelength of 254 nm.

Referring to FIGS. 12-34, the portable sanitizing system 1100 can be used to safely and effectively sanitize high-touch surfaces in the flight deck and internal cabin in a timely and cost-effective manner. UV disinfection allows the internal cabin to be quickly and effectively disinfected, such as between flights. In at least one embodiment, the portable sanitizing system 1100 is used to augment a cleaning process, such as after manual cleaning.

Figure 35:
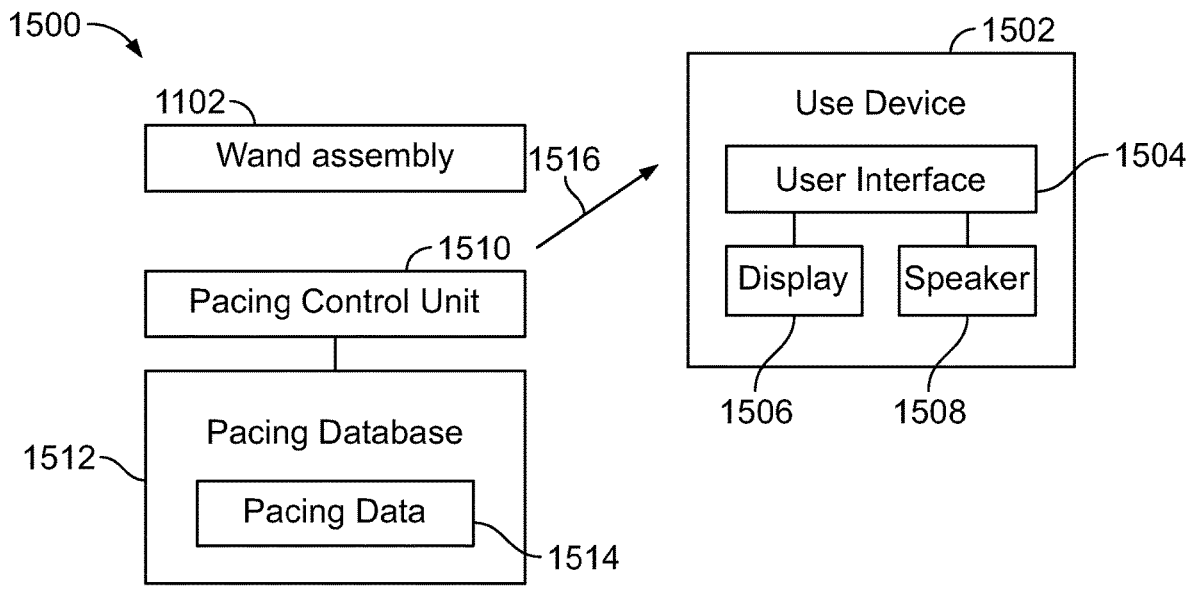
FIG. 35 illustrates a schematic block diagram of a UV light pacing system, according to an embodiment of the present disclosure.

FIG. 35 illustrates a schematic block diagram of a UV light pacing system 1500, according to an embodiment of the present disclosure. The UV light pacing system 1500 includes the wand assembly 1102, such as part of the UV sanitizing system 1100 (shown in FIG. 12). The wand assembly 1102 includes a sanitizing head, as described herein. The sanitizing head includes a UV lamp that is configured to emit sanitizing UV light, such as having a wavelength between 200-230 nm or between 230 nm-280 nm. The wand assembly 1102 may include a handle that allows the sanitizing head to move relative to the handle. Optionally, the wand assembly 1102 may include a sanitizing head and handle that are fixed in relation to one another.

The UV light pacing system 1500 also includes a user device 1502. The user 1502 is an example of the user device 154 shown in FIG. 1. In at least one embodiment, the user device 1502 is a handheld device, such as a smart phone or smart tablet. As another example, the user device 1502 may be a computer, such as a desktop or laptop computer.

The user device 1502 includes a user interface 1504, a display 1506, and a speaker 1508, such as a speaker formed on or in, or otherwise coupled to the user device 1502, or a headphone(s) coupled to the user device 1502 via a wired or wireless connection. The user interface 1504 includes an input device, such as a keyboard, mouse, or the like. The display 1506 includes a monitor or screen. In at least one embodiment, the user interface 1504 and the display 1506 are integrated as a touchscreen interface.

A pacing control unit 1510 is in communication with the user device 1502, such as through one or more wired or wireless connections. The pacing control unit 150 shown and described with respect to FIG. 1 may include the pacing control unit 1510, or vice versa. The pacing control unit 1510 may be in communication with the user device 1502 through Bluetooth, WiFi, and/or Internet connectivity. The pacing control unit 1510 may be remotely located from the user device 1502. In at least one other embodiment, the user device 1502 may include the pacing control unit 1510. For example, the pacing control unit 1510 may be contained within a housing of the user device 1502.

The pacing control unit 1510 is also in communication with a pacing database 1512, which stores pacing data 1514, such as through one or more wired or wireless connections. The pacing database 160 shown and described with respect to FIG. 1 may include the pacing database 1512, or vice versa. The pacing control unit 1510 may be in communication with the pacing database 1512 through Bluetooth, WiFi, and/or Internet connectivity. The pacing control unit 1510 may be remotely located from the pacing database 1512. In at least one other embodiment, the pacing control unit 1510 may be co-located with the pacing database 1512. For example, the pacing control unit 1510 and the pacing database 1512 may be contained within a common computer workstation. As another example, the pacing control unit 1510 and the pacing database 1512 may be contained within the user device 1502.

The pacing database 1512 stores pacing data 1514 regarding one or more items to be disinfected. Pacing information regarding a selected item for disinfection is determined from the pacing data 1514. For example, the pacing data 1514 includes pacing information regarding numerous items to be disinfected. The pacing data 1514 may include the surface disinfection data 162 shown and described with respect to FIG. 1, or vice versa. An item to be disinfected is selected through the user device 1502, and the pacing control unit 1510 analyzes the pacing data 1514 to determine the pacing information for the item, as stored within the pacing data 1514.

The pacing data 1514 may include information regarding ultraviolet (UV) disinfecting information for various items (such as surfaces, components, and the like) and/or pathogens. For example, the pacing data 1514 includes UV disinfecting dosage for a particular item in relation to a particular pathogen to neutralize.

In operation, a user communicates with the pacing control unit 1510 through the user device 1502. The user may select an item to be disinfected. The pacing control unit 1510 analyzes the item for disinfection by reviewing the pacing data 1514 stored in the pacing database 1512. The pacing control unit 1510 then outputs a pacing signal 1516 that includes pacing information for disinfecting the item to the user device 1502. At least a portion of the pacing information may be shown on the display. The pacing information may include a distance to a surface of the item, time for disinfecting, and a rate at which the wand assembly 1102 should be swept over or otherwise moved in relation to the item. The pacing information may also include a pacing audio signal that is broadcast through the speaker 1508. The pacing audio signal, as broadcast by the speaker 1508, is an audio cue that allows the user to synchronize the pace of sweeping or otherwise moving the wand assembly 1102. In this manner, the pacing control unit 1510 allows the user to effectively and efficiently disinfect the item.

As described herein, the UV light pacing system 1500 includes the wand assembly 1102 including a UV lamp that is configured to emit UV light. The user device 1502 is configured to allow a user to select an item to be disinfected with the UV light. The pacing control unit 1510 is in communication with the user device 1502. The pacing control unit 1510 is configured to output the pacing signal 1516 to the user device 1502. The pacing signal 1516 includes pacing information regarding operation of the wand assembly 1102 to disinfect the item. For example, the pacing information includes instructions (which are shown on the display 1506) for operating the wand assembly 1102 to disinfect the item. As another example, the pacing information includes one or more audio cues (which are broadcast by the speaker 1508) for pacing motion of the wand assembly 1102 during a disinfection process of the item. In at least one embodiment, the pacing information includes both the instructions, as shown on the display 1506, and the audio cues, as broadcast by the speaker 1508.

In at least one embodiment, the pacing data 1514, which includes the pacing information, is saved in the pacing database 1512. The pacing control unit 1510 is configured to analyze the stored pacing data 1514. Further, the pacing data 1514 can be shared with others at any time. For example, the pacing data 1514 can be saved with respect to a complete maintenance record and history of UV exposure. The pacing data 1514 can be reviewed to determine which areas to prioritize for disinfecting. In at least one embodiment, the pacing data 1514 can be saved along with sensor data for robot or human performance feedback contemporaneously or later. The sensor data can be basic, simple data to reduce data storage requirements, or as complex, such as video data showing a cleaning process. In this manner, the pacing data 1514 may provide feedback information regarding surfaces that have been cleaned, the effectiveness of such cleaning, and surfaces that need to be cleaned.

Figure 36:
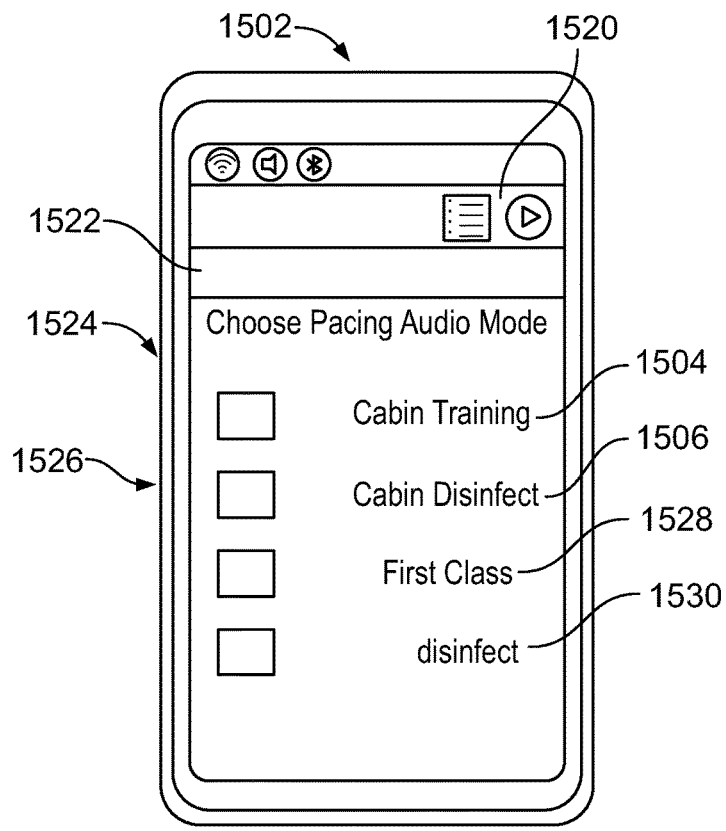
FIG. 36 illustrates a front view of a user device, according to an embodiment of the present disclosure.

FIG. 36 illustrates a front view of the user device 1502, according to an embodiment of the present disclosure. As shown, the user device 1502 is a handheld smart device (such as a smart phone or smart tablet) that includes a touchscreen interface 1520 that integrates the user interface 1504 and the display 1506.

Referring to FIGS. 35-36, the pacing control unit 1510 shows a pacing menu screen 1522 on the user device 1502. The pacing menu screen 1522 allows a user to select a particular pacing mode. For example, the pacing menu screen 1522 shows a first training option 1524, such as for a cabin of a particular type of aircraft, and a disinfecting pacing option 1526 for the cabin. The pacing menu screen 1522 may also show a second training option 1528, such as for a different area within the aircraft, and a disinfecting pacing option 1530 for the different area.

The pacing control unit 1510 provides the training options and disinfecting pacing options to provide the user audio cures to provide a correct of amount of time for exposure of areas within the aircraft to disinfecting UV light, as emitted by the wand assembly 1102. As such, the user may pace movement of the wand assembly 1102 during sanitation, such as via the audio signals broadcast by the pacing control unit 1510 through the speaker 1508, to ensure a correct disinfecting dose of UV light in mJ/cm2.

The pacing information, as included in the pacing signal 1516 output by the pacing control unit 1510 to the user device (and as show on the display 1506 and/or broadcast through the speaker 1508) includes a range of the wand assembly 1102 to a surface to be disinfected, a time of UV illumination of the surface, and a rate of sweep of the wand assembly 1102 (such as a rate for sweeping the wand assembly 1102 back and forth over the surface). In at least one embodiment, the rate of sweep is guided by an audio signal broadcast through the speaker 1508 and/or through visual cues as provided by alterations of the ranging light 131 (shown in FIG. 1).

The training options may include audio files for a pace of sweeping or otherwise moving the wand assembly 1102 and detailed instructions to ensure effective and efficient sanitation of items. A user can listen to such audio files to learn the proper sweep rate of the wand assembly 1102 for a particular item or items. The disinfecting pacing options may include audio files for a pace of sweeping or otherwise moving the wand assembly 1102 without detailed instructions.

Figure 37:
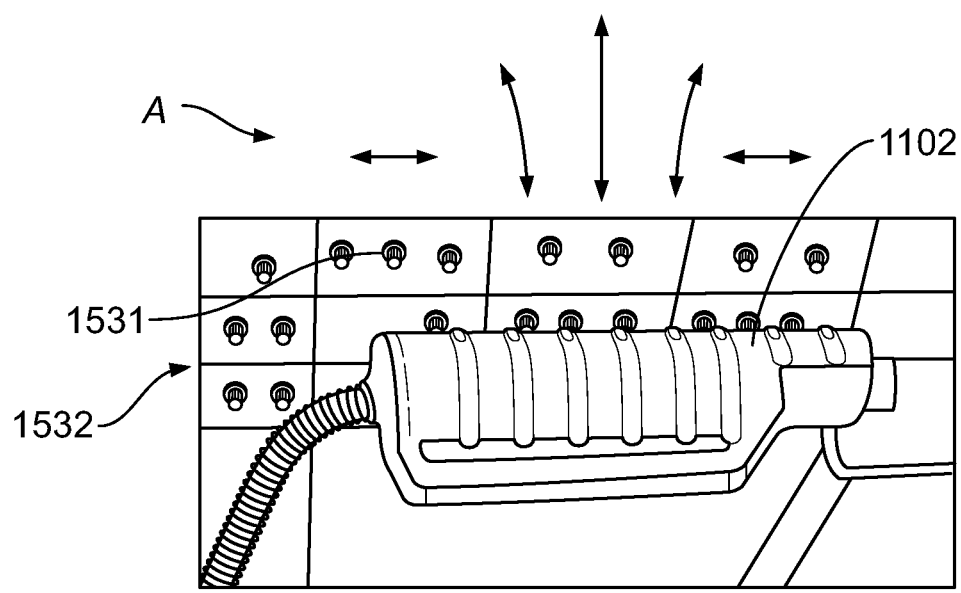
FIG. 37 illustrates a perspective view of a wand assembly in relation to controls within a flight deck, according to an embodiment of the present disclosure.

FIG. 37 illustrates a perspective view of the wand assembly 1102 in relation to controls 1531 within a flight deck 1532, according to an embodiment of the present disclosure. The controls 1531 are one example of items to be disinfected by UV light. Other examples include seats, stowage bin assemblies, walls, ceilings, galley carts, counters, cabinets, toilets, sinks, floors, and/or the like. The wand assembly 1102 is spaced apart from the controls 1531 a particular range, as noted in the pacing information, and swept in various directions in relation to the controls 1531, such as in the directions of arrows A.

Referring to FIGS. 35-37, a user selects the item(s) that is to be disinfected via the user device 1502. The pacing control unit 1510 retrieves the pacing data 1514 regarding the selected item(s) from the pacing database 1512. The pacing control unit 1510 then outputs the pacing signal 1516 that includes the pacing information for the item(s) (such as the controls 1531) to the user device 1502. The pacing information, as shown on the display 1506 and/or broadcast through the speaker 1508, assists the user with sweeping the wand assembly 1102 in relation to the item(s) to effectively and efficiently sanitize and disinfect the item(s).

Figure 38:
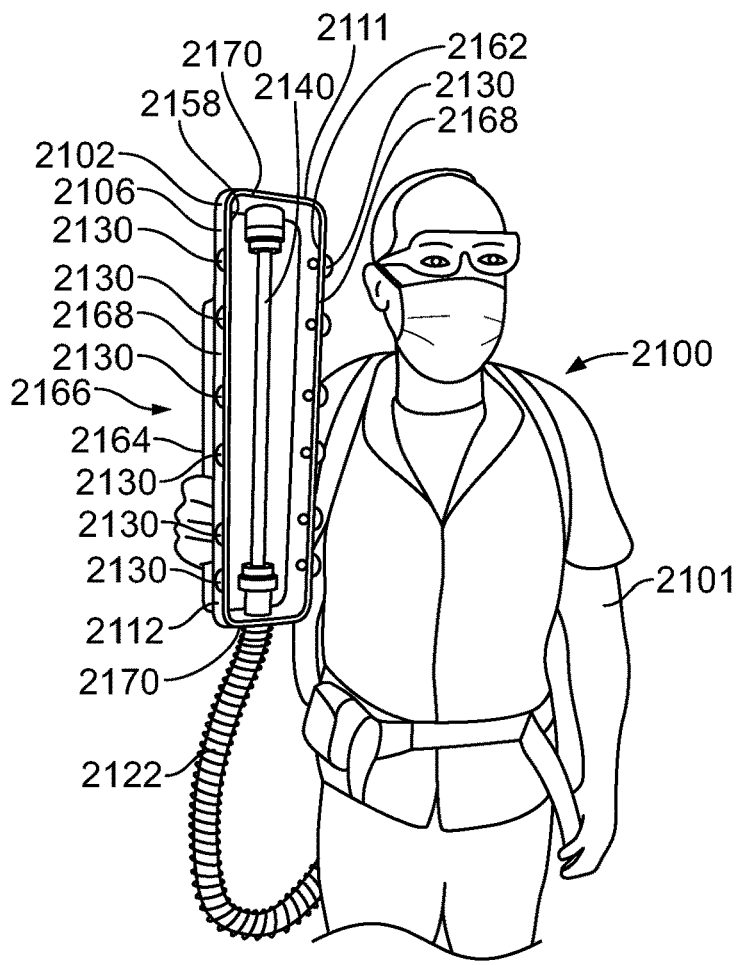
FIG. 38 illustrates an embodiment of the portable sanitizing system of the present disclosure worn by an individual.

FIG. 38 depicts another embodiment of a portable sanitizing system 2100 worn by an individual or user 2101. In the illustrated embodiment, the wand assembly 2102 lacks a handle coupled to the sanitizing head 2106. The wand assembly 2102 is an example of the wand assembly 102 shown in FIG. 1. The sanitizing head 2106 has a handle 2164 that is an integral feature of the housing 2111. For example, the handle 2164 may be fixed to a rear 2166 of the shroud 2112. The other components of the portable sanitizing system 2100 shown in FIG. 38 may be the same or similar as described above. In FIG. 38, the cover plate and the bumper are omitted for descriptive purposes.

The range light sources 2130 are disposed on the housing 2111 and used to help the user 2101 maintain a desired range to the target surface of the structure being sanitized. The range light sources 2130 are examples of the range light sources 130 shown and described with respect to FIG. 1, for example. The range light sources 2130 may be light emitting diodes (LEDs). In the illustrated embodiment, the range light sources 2130 are mounted to the shroud 2112 at or proximate to the exposed perimeter edge 2158. For example, the range light sources 2130 may contact the interior surface 2162 of the shroud 2112. Alternatively, the range light sources 2130 may be mounted to other parts of the housing 2111, such as the rim and/or the cover plate.

The exposed perimeter edge 2158 of the shroud 2112 has a rectangular shape that includes two longer segments 2168 and two shorter segments 2170. As the names imply, the longer segments 2168 have greater lengths than the shorter segments 2170. The longer segments 2168 extend along both sides of the UV lamp 2140 such that the UV lamp 2140 is between the two longer segments 2168. A length axis of the UV lamp 2140 is parallel to the longer segments 2168. In the illustrated embodiment, the range light sources 2130 are located on both of the longer segments 2168 of the exposed perimeter edge 2158 and are not located on the shorter segments 2170. The multiple range light sources 2130 are disposed on each longer segment 2168 to define two parallel lines or rows 2174 (shown in FIG. 39) of light sources 2130. In one or more other embodiments, the range light sources 2130 are also mounted to the shorter segments 2170 and/or may be mounted at corners between the shorter and longer segments 2168, 2170.

Figure 39:
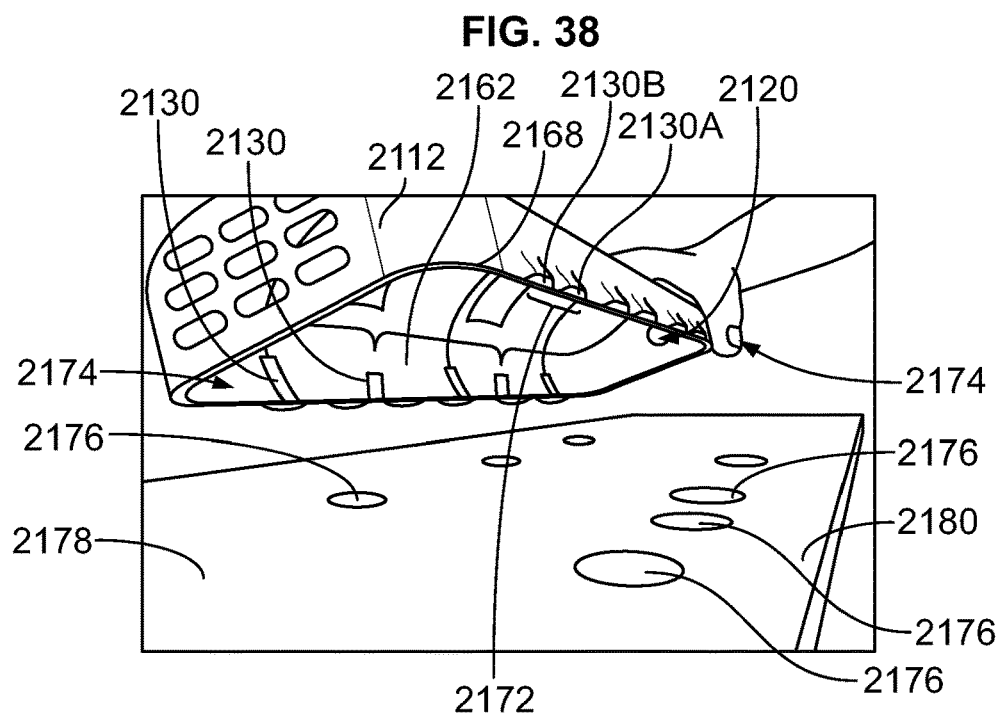
FIG. 39 illustrates a front perspective view of a shroud and range light sources, according to an embodiment of the present disclosure.
Figure 40:
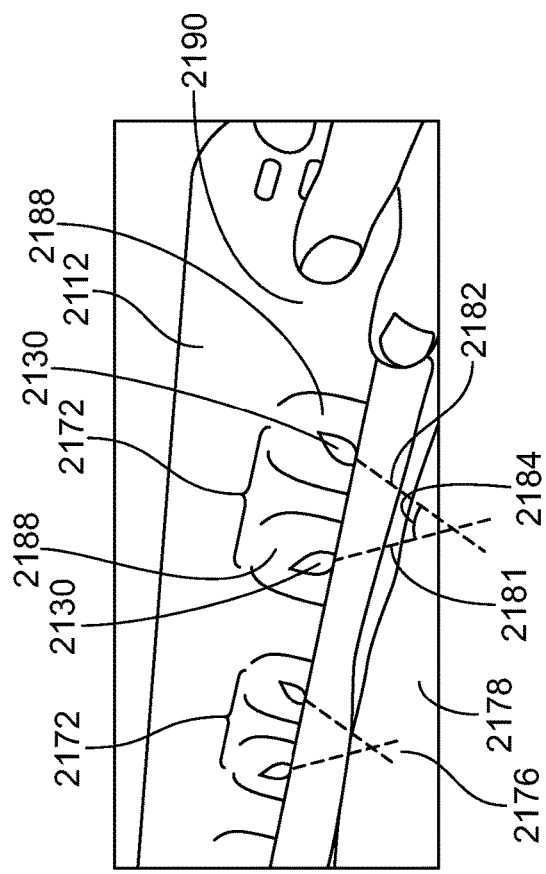
FIG. 40 is a side perspective view of a portion of the shroud and the range light sources shown in FIG. 39.

FIG. 39 is a front perspective view of the shroud 2112 and the range light sources 2130 according to an embodiment. FIG. 40 is a side perspective view of a portion of the shroud 2112 and the range light sources 2130 shown in FIG. 39. The shroud 2112 may be at least partially translucent such that light emitted from the range light sources 2130 located inside the shroud 2112 is visible through the thickness of the shroud 2112, as shown in FIGS. 39 and 40.

Referring to FIG. 39, the range light sources 2130 are spaced apart from each other along the two parallel rows 2174. The range light sources 2130 may be light emitting diodes (LEDs). The conductive wires and other hardware may be routed along the interior surface 2162 of the shroud 2112 and exit through the port 2120 into the hose 2122 (shown in FIG. 38) to connect to an electrical power source, such as a battery in the backpack assembly. The LEDs may be narrow divergence LEDs that have a divergence no greater than 10 degrees. As shown in FIG. 40, each range light source 2130 emits respective light or light beam forward of the shroud 2112 that illuminates a nearby structure 2180 to form a respective light marker 2176 (for example, ranging light 131) on the target surface 2178 of the structure 2180. The light markers 2176 in FIG. 40 are approximately circular or ellipsoidal in shape.

Referring to FIG. 40, the range light sources 2130 are arranged in one or more pairs 2172. In the illustrated embodiment, there are multiple pairs 2172, but only a single pair 2172 of range light sources 2130 may be utilized in a basic embodiment. The range light sources 2130 in each pair 2172 are oriented relative to each other to emit respective light beams that converge at a predetermined distance in front of the UV lamp 2140 (shown in FIG. 38). For example, the two range light sources 2130 in each pair 2172 may be angled towards each other such that an aiming axis 2181 of the first range light source 2130 and an aiming axis 2182 of the second range light source 2130 in the pair 2172 intersect at the predetermined distance. The light beams are emitted generally along the respective aiming axes 2181, 2182. The range light sources 2130 in the pair 2172 may be oriented relative to each other at an angle 2184 (defined between the axes 2181, 2182) that is in a range between 10 degrees and 80 degrees. The angle 2184 may be between 20 degrees and 60 degrees. The angle 2184 is determined based on the intended sanitizing application and the known characteristics of the UV light that is emitted. More specifically, the angle 2184 is determined such that the convergence occurs at a designated distance in front of the UV lamp that corresponds to a desired proximity of the UV lamp to the target surface which yields effective disinfection.

The two range light sources 2130 in each pair 2172 may emit different colored light in order to visually distinguish between the light emitted from the different light sources 2130. For example, the light marker 2176 in FIG. 39 emitted by a first range light source 2130A of a pair 2172 may be a difference color than the light marker 2176 emitted by a second range light source 2130B of the pair 2172. In an example, the first range light source 2130A may emit blue or green light, and the second range light source 2130B may emit amber, yellow, orange, or red light.

As shown in FIGS. 39 and 40, the two range light sources 2130 in each pair 2172 are adjacent to each other and located on a common segment 2168 of the shroud 2112. The two light sources 2130 in each pair 2172 may be separated by a discrete spacing distance, such as 1 inch, 2 inches, 3 inches, 4 inches, or the like. The spacing distance also affects the relative angle 2184 at which the light sources 2130 are oriented in order to provide converging light at a designated distance in front of the UV lamp 2140. In the illustrated embodiment, the shroud 2112 includes three discrete pair 2172 of range light sources 2130 on each of the two longer segments 2168, for a total of twelve range light sources 2130. The number and arrangement of the range light sources 2130 may be based on the dimensions of the shroud 2112 such that more or fewer light sources 2130 can be used in other embodiments. Optionally, the shroud 2112 may include molded bulges 2188 along the exterior surface 2190 of the shroud 2112 at the locations of the range light sources 2130. The bulges 2188 protrude outward to provide individual spaces for the range light sources 2130 within the shroud 2112.

Figure 41:
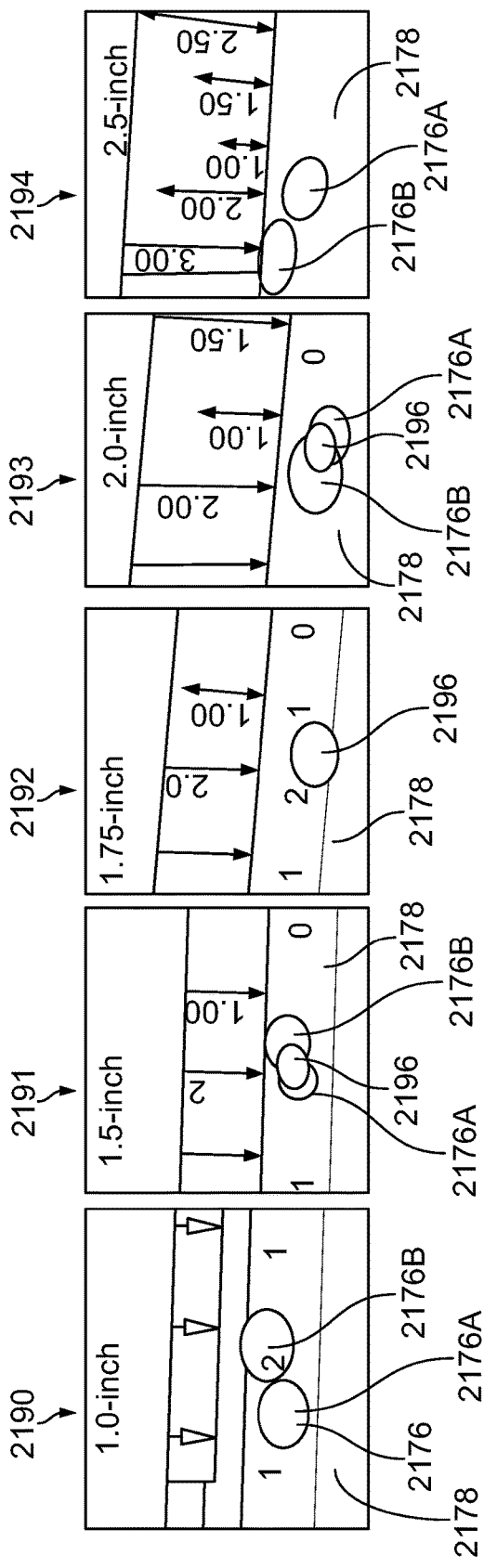
FIG. 41 depicts five images showing light markers emitted by a pair of range light sources from different distances relative to a target surface, according to an embodiment of the present disclosure.

FIG. 41 depicts five images 2190-2194 showing the light markers 2176 emitted by a pair 2172 of range light sources 2130 from different distances relative to a target surface 2178. FIG. 41 shows how the relative positioning of the light markers 2176 can provide guidance to a user concerning whether the sanitizing head 2106 is located at a desired distance from the target surface 2178 to provide effective disinfection. For example, the first image 2190 shows the light markers 2176 at a distance of 1.0 inch from the surface 2178. The second image 2191 shows the light markers 2176 at a distance of 1.5 inches from the surface 2178. The third image 2192 shows the light markers 2176 at a distance of 1.75 inches from the surface 2178. The fourth image 2193 shows the light markers 2176 at a distance of 2.0 inches from the surface 2178, and the fifth image 2194 shows the light markers 2176 at a distance of 2.5 inches from the surface 2178. The distances may be refer to the distance between the UV lamp 2140 and the area of the target surface 2178 that is illuminated by the UV light emitted by the UV lamp 2140. The light markers 2176 include a first light marker 2176A and a second light marker 2176B that have different colors and are emitted by different range light sources 2130 in a single pair 2172. For example, the first light marker 2176A may be amber, and the second light marker 2176B may be blue.

In the illustrated embodiment, the two range light sources 2130 in the pair 2172 are intentionally oriented for the light beams emitted from the light sources to converge at a distance of 1.75 inches. That convergence distance may be determined based on characteristics of the UV light and/or disinfecting properties. For example, the convergence distance may represent a distance in which the UV light provides desirable sanitization to kill or neutralize pathogens. When the sanitizing head 2106 is held too close to the target surface 2178, such as at 1.0 inches as shown in image 2190, the first and second markers 2176A, 2176B are generally discrete with little or no overlap. The lack of overlap is visible to the user which indicates that the sanitizing head is not in correct position. The user moves the sanitizing head 2106 closer or farther from the surface 2178 to cause the markers 2176A, 2176B to move together. In this case, moving the sanitizing head 2106 farther away to 1.5 inches as shown in image 2191 causes the markers 2176A, 2176B to partially converge and define an overlap region 2196. The overlap region 2196 is the area that is concurrently illuminated by both of the range image sources 2130 in the pair 2172. The overlap region 2196 may have a different color than the individual markers 2176A, 2176B, such as a lighter or whiter color. As the sanitizing head 2106 is moved even farther away from the surface 2178, the size of the overlap region 2196 increases until the distance reaches 1.75 inches as shown in image 2192. In image 2192, the two markers 2176A, 2176B almost completely overlap such that there is essentially only one light marker now instead of two. This large overlap region 2196 (e.g., and the singular marker) indicate to the user that the sanitizing head 2106 is positioned at a desirable height or distance from the target surface 2178 to provide effective disinfecting.

Additional movement of the sanitizing head 2106 away from the target surface 2178 causes the overlap region 2196 to shrink as the discrete amber and blue light markers 2176A, 2176B become visible and move apart from each other, which is shown in images 2193 and 2194. Although the visual cues shown in images 2190 and 2194 look similar, the user can quickly determine if the sanitizing head 2106 should be moved closer or farther from the target surface 2178 to achieve the desired positioning by moving the sanitizing head 2106 closer or farther from the surface 2178 and observing whether the individual markers 2176A, 2176B move closer together or farther away. If the markers 2176A, 2176B diverge even more, then that indicates that the sanitizing head 2106 should be moved in the opposite direction.

Figure 42:
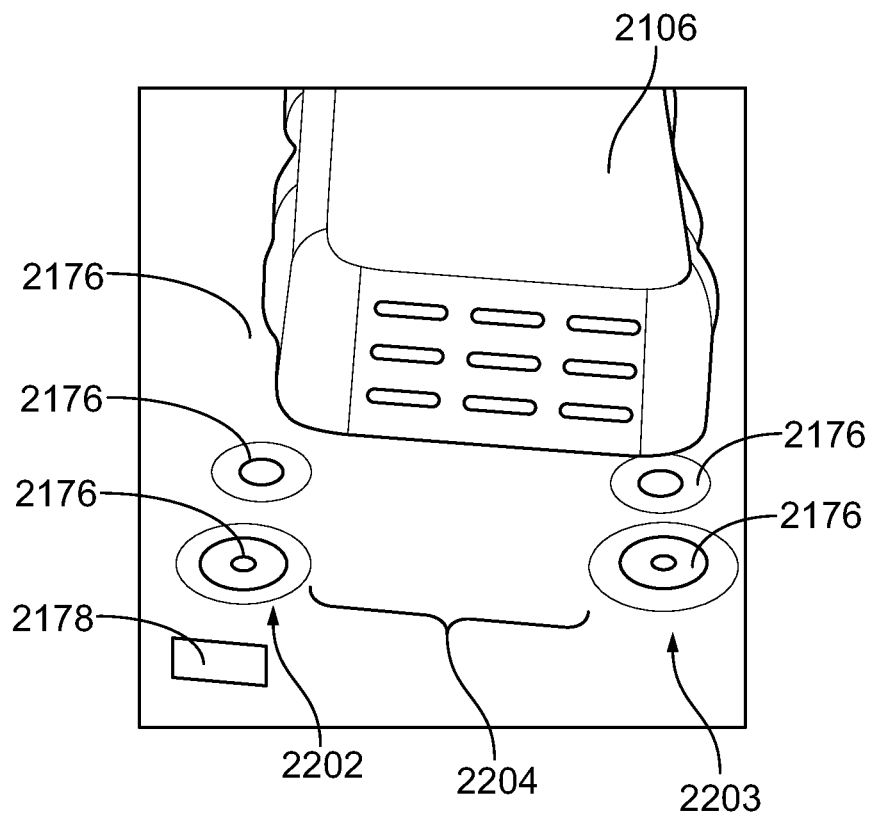
FIG. 42 is an end view of the sanitizing head showing the light markers on the target surface that is being sanitized, according to an embodiment of the present disclosure.
Figure 43:
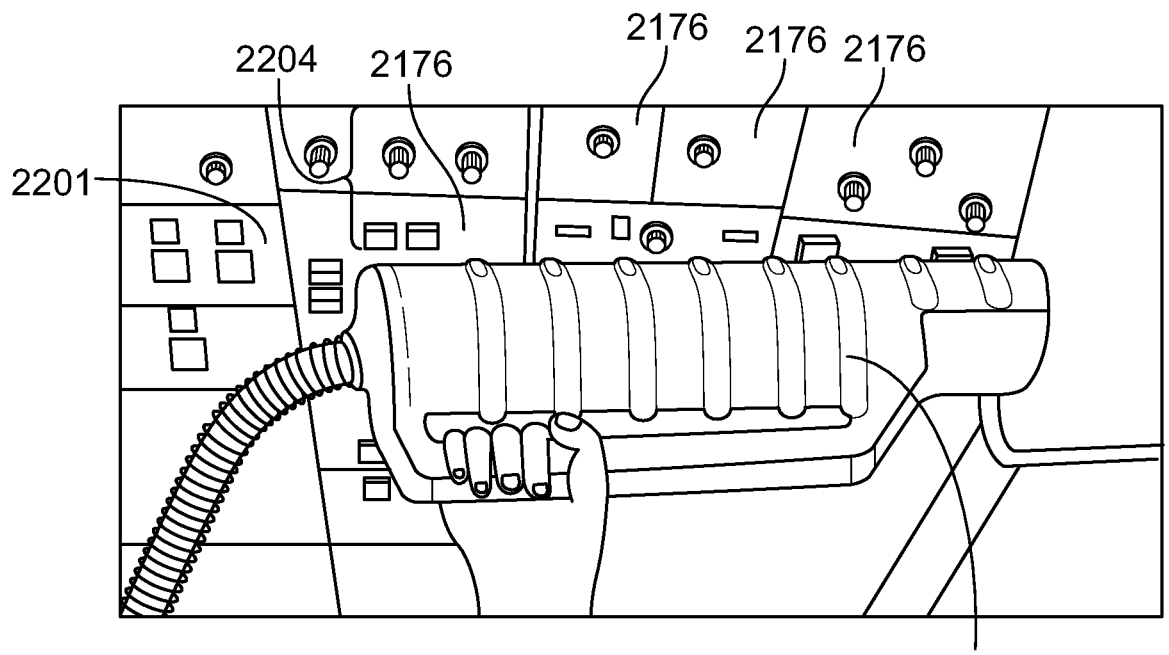
FIG. 43 is a side perspective view showing the sanitizing head used to sanitize and disinfect an instrument panel, according to an embodiment of the present disclosure.

FIG. 42 is an end view of the sanitizing head 2106 showing the light markers 2176 on the target surface 2178 that is being sanitized. FIG. 43 is a side perspective view showing the sanitizing head 2106 used to sanitize and disinfect an instrument panel 2201. The light markers 2176 illuminate the target surface 2178 in two parallel rows 2202, 2203. The two rows 2202, 2203 can provide a visual indication to the user of the area that is being disinfected. For example, the intervening area 2204 between the two rows 2202, 2203 is illuminated with UV light from the UV lamp 2140. In addition to provided range guidance in the depth dimension, by bordering or framing the UV illuminated area 2204, the range light sources 2130 help the user determine which section of the target surface 2178 is receiving a dose of UV radiation (e.g., is being disinfected) at any given time. The user may not be able to see the UV light itself.

Figure 44:
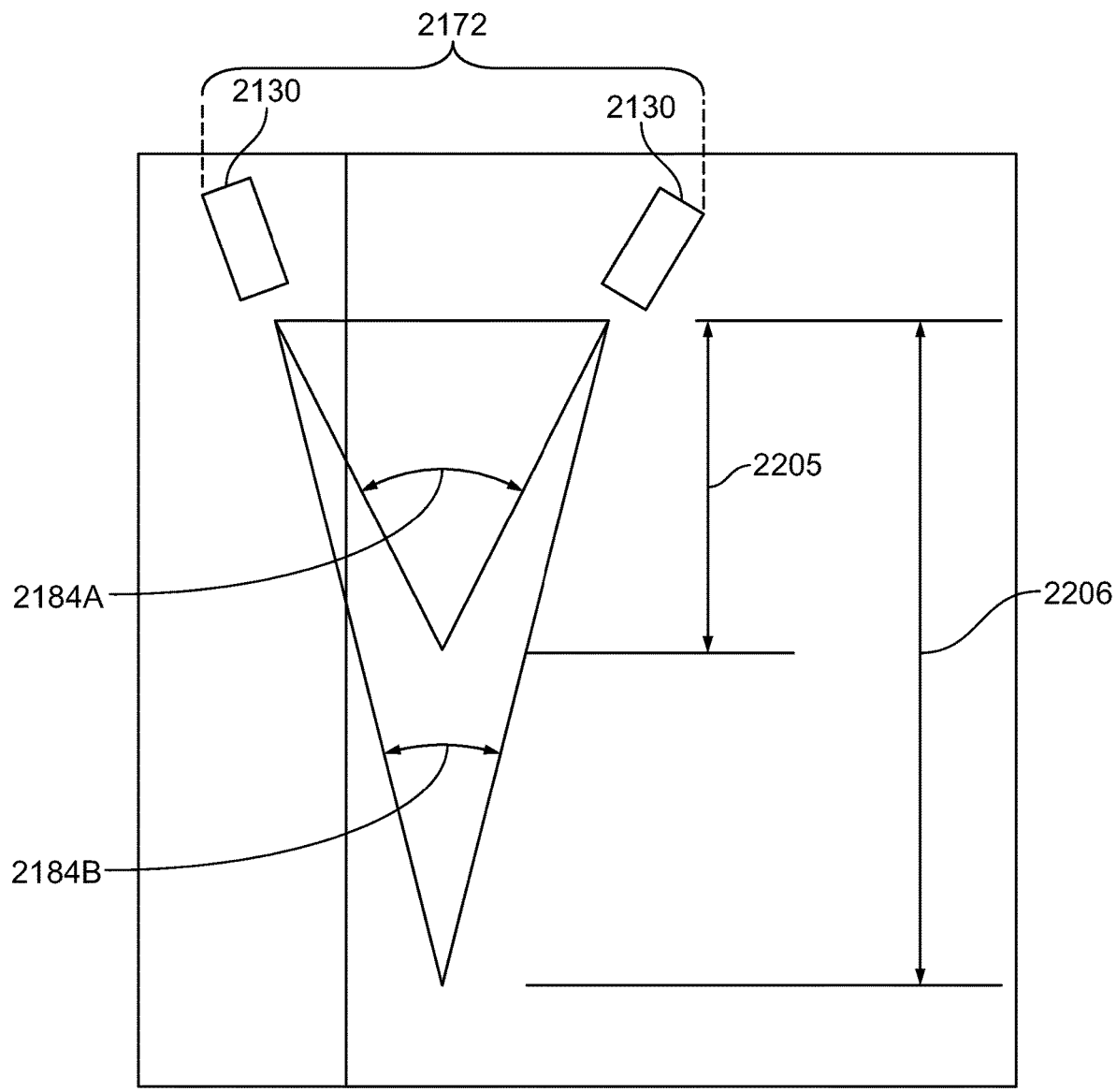
FIG. 44 is a diagram showing multiple relative angles between two range light sources in a pair, according to an embodiment of the present disclosure.

FIG. 44 is a diagram showing multiple relative angles between the two range light sources 2130 in a pair 2172 according to an embodiment. The LEDs used for the range light sources 2130 may have a narrow divergence of 8 to 10 degrees. The relative angle 2184A, 2184B in the housing 2111 is predetermined based on the type of UV lamp 2140 used and the intended use of the disinfecting system. For example, when disinfecting flat surfaces, such as a cabin area within a vehicle, a desirable distance between the 222 nm UV lamp 140 and the target surface may be between 1 and 3 inches, inclusive of the end points. In an embodiment, the desirable distance may be approximately 2 inches. Based on a predetermined separation distance between each other, the range light sources 2130 in the pair 2172 may be set at an angle of approximately 53 degrees from one another. At this angle, the light beams emitted from the two light sources 2130 will converge at a distance in front of the sanitizing head 2106 that matches the desired distance, such as 2 inches. Therefore, when the markers converge at the overlap region as shown in image 2192 of FIG. 41, that indicates to the user that the sanitizing head 2106 is at the correct distance 2205 from the target surface for the intended application.

When disinfecting surfaces with protrusions, such as a flight deck of an aircraft, a desirable distance between the 222 nm UV lamp 2140 and the target surface may be between 3 and 6 inches, inclusive of the end points. The desirable distance 2206 may be approximately 4 inches (e.g., within 5%, 10%, or 15% of 4.0 inches). At the same predetermined separation distance, the range light sources 2130 in the pair 2172 may be set at an angle of approximately 28 degrees from one another. At this angle, the light beams emitted from the two light sources 2130 will converge at a distance in front of the sanitizing head 2106 that matches the desired distance, such as 4 inches. Therefore, when the markers converge at the overlap region as shown in image 2192 of FIG. 41, that indicates to the user that the sanitizing head 2106 is at the correct distance 2206 from the target surface for the intended application.

Figure 45:
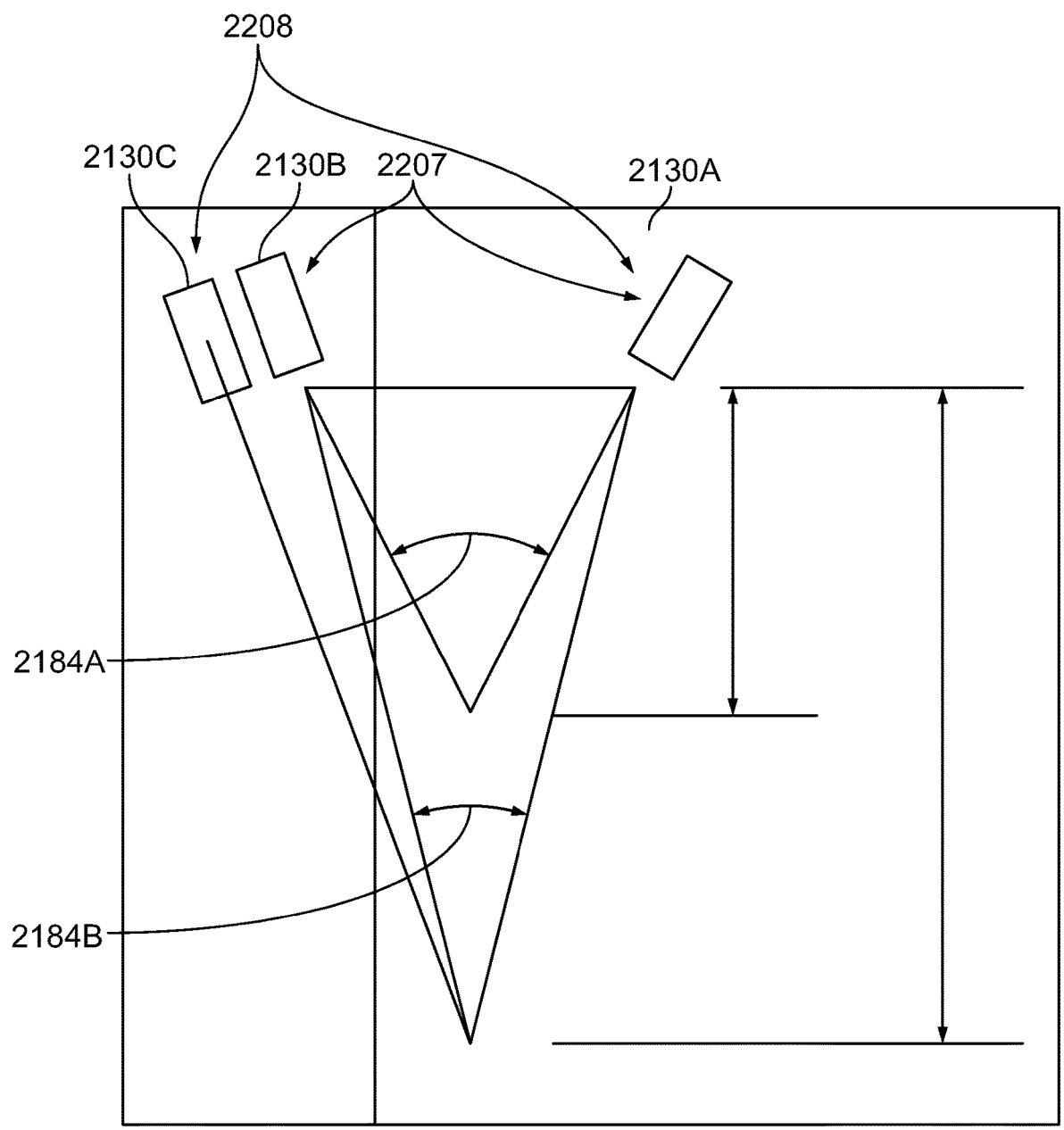
FIG. 45 is a diagram showing three range light sources, according to an alternative embodiment of the present disclosure.

FIG. 45 is a diagram showing three range light sources 2130 according to an alternative embodiment. The sanitizing head 2106 may include at least one pair of range light sources 2130 arranged in a first subset 2207 and at least one pair of range light sources 2130 arranged in a second subset 2208. Each of the subsets 2207, 2208 may include one pair or multiple pairs of range light sources 2130. The pairs in the first subset 2207 are oriented at a different relative angle than the pairs in the second subset 2208. For example, the pairs in the first subset 2207 may have a first relative angle 2184A that is approximately 53 degrees, and the pairs in the second subset 2207 may have a second relative angle 2184B that is approximately 28 degrees. The range light sources 2130 may be selectively controlled via the user or an automated control system to operate the first subset 2207 without the second subset 2208 for a first intended application and to operate the second subset 2208 without the first subset 2207 for a second intended application. The first intended application could be to clean a cabin area within a vehicle, and the second intended application could be to clean a flight deck of an aircraft.

Optionally, at least one range light source 2130 can define part of two different pairs. For example, the illustrated diagram shows a first range light source 2130A, a second range light source 2130B, and a third range light source 2130C. The second and third range light sources 2130B, 2130C may emit the same colored light, such as blue light. The first range light source 2130A defines a pair in the first subset 2207 with the second range light source 2130B. The first range light source 2130A defines a pair in the second subset 2208 with the third range light source 2130C. The third range light source 2130C represents one of an alternate set of LEDs along one side of the housing 2111. The second and third range light sources 2130B, 2130C are disposed on the same side of the housing 2111 but set at different angles to allow the user to switch the optimum disinfecting distance based on the intended use. A switch can be installed to change the focus from 2 inches to 4 inches depending upon the desired range (switching from blue LED1 to blue LED2) without changing the red LED 2130A.

As described herein, embodiments of the present disclosure provide systems and methods for efficiently sterilizing surfaces, such as within an internal cabin of a vehicle. Further, embodiments of the present disclosure provide mobile, compact, easy-to-use, consistent, reliable, and safe systems and methods for using UV light to sterilize surfaces within an internal cabin.

Further, the disclosure comprises embodiments according to the following clauses:

Clause 1. An ultraviolet (UV) light pacing system, comprising:
- an assembly (such as a wand assembly) including a UV lamp configured to emit UV light to disinfect a component; and
- one or more range light sources configured to emit ranging light,
- wherein at least one aspect of the ranging light is altered to provide a visual cue for guiding motion of the assembly to disinfect the component.

Clause 2. The UV light pacing system of Clause 1, wherein the one or more range light sources are secured to the assembly.

Clause 3. The UV light pacing system of Clauses 1 or 2, wherein the at least one aspect comprises one or more of duration of emission of the ranging light, frequency of emission of the ranging light, color of the ranging light, or intensity of ranging light.

Clause 4. The UV light pacing system of any of Clauses 1-3, wherein the UV lamp is configured to emit the UV light having a wavelength between 200 nm-230 nm.

Clause 5. The UV light pacing system of any of Clauses 1-4, wherein the UV lamp is configured to emit the UV light having a wavelength of 222 nm.

Clause 6. The UV light pacing system of any of Clauses 1-3, wherein the UV lamp is configured to emit the UV light having a wavelength between 230 nm-280 nm.

Clause 7. The UV light pacing system of any of Clauses 1-3 or 6, wherein the UV lamp is configured to emit the UV light having a wavelength of 254 nm.

Clause 8. The UV light pacing system of any of Clauses 1-7, further comprising a pacing control unit in communication with the one or more range light sources, wherein the pacing control unit is configured to operate the one or more range light sources to alter the at least one aspect of the ranging light.

Clause 9. The UV light pacing system of Clause 8, wherein the assembly includes the pacing control unit.

Clause 10. The UV light pacing system of Clauses 8 or 9, further comprising a pacing database in communication with the pacing control unit, wherein the pacing database stores surface disinfection data for one or more surfaces of one or more components.

Clause 11. The UV light pacing system of Clause 10, wherein the pacing control unit shows surface disinfection information regarding the surface disinfection data for the component on a display of a user device.

Clause 12. The UV light pacing system of Clauses 10 or 11, wherein the pacing database further stores map data regarding at least one map of an environment, wherein the at least one map divides at least a portion of the environment into a plurality of zones, and wherein each of the plurality of zones is associated with respective surface disinfection data.

Clause 13. The UV light pacing system of any of Clauses 1-12, further comprising a user device including a display and a selector.

Clause 14. The UV light pacing system of Clause 13, wherein the selector is configured to allow selection of a time period for at least a portion of the visual cue.

Clause 15. The UV light pacing system of Clauses 13 or 14, wherein the assembly comprises the user device.

Clause 16. The UV light pacing system of any of Clauses 1-15, further comprising a navigation sub-system configured to track a location of the assembly within an environment.

Clause 17. The UV light pacing system of Clause 16, further comprising a pacing control unit in communication with the assembly and the navigation sub-system, wherein the pacing control unit, based on the location of the assembly in relation to the component within the environment, automatically determines surface disinfection data for the component.

Clause 18. The UV light pacing system of any of Clauses 1-17, further comprising an augmented reality sub-system in communication with the assembly and a pacing control unit, wherein the pacing control unit automatically shows one or both of surface disinfection data regarding the component or one or more visual indications for moving the assembly to disinfect various surfaces on a portion of the augmented reality sub-system as an operator moves through an environment.

Clause 19. The UV light pacing system of any of Clauses 1-18, wherein the assembly further comprises a cover that covers the UV lamp, wherein the cover is one of a wire mesh screen or a stamped or laser cut metal sheet with formed apertures.

Clause 20. An ultraviolet (UV) light pacing method, comprising:
emitting ranging light from one or more range light sources of an assembly having a UV lamp configured to emit UV light to disinfect a component; and
altering at least one aspect of the ranging light to provide a visual cue for guiding motion of the assembly to disinfect the surface of the component.

Clause 21. The UV light pacing method of Clause 20, further comprising:
communicatively coupling a pacing control unit with the one or more range light sources; and
operating, by the pacing control unit, the one or more range light sources to alter the at least one aspect of the ranging light.

Clause 22. The UV light pacing method of Clause 21, further comprising:
communicatively coupling a pacing database in communication with the pacing control unit; and
storing, within the pacing database, surface disinfection data for one or more surfaces of one or more components.

Clause 23. The UV light pacing method of Clause 22, further comprising showing, by the pacing control unit, surface disinfection information regarding the surface disinfection data for the component on a display of a user device.

Clause 24. The UV light pacing method of Clauses 22 or 23, further comprising storing, within the pacing database, map data regarding at least one map of an environment, wherein the at least one map divides at least a portion of the environment into a plurality of zones, and wherein each of the plurality of zones is associated with respective surface disinfection data.

Clause 25. The UV light pacing method of any of Clauses 20-24, further comprising selecting, via a selector of a user interface a time period for at least a portion of the visual cue.

Clause 26. The UV light pacing method of any of Clauses 20-25, further comprising:
using a navigation sub-system to track a location of the assembly within an environment; and
determining, by a pacing control unit in communication with the assembly and the navigation sub-system, surface disinfection data for the component based on the location of the assembly in relation to the component within the environment.

Clause 27. The UV light pacing method of any of Clauses 20-26, further comprising:
communicatively coupling an augmented reality sub-system with the assembly and a pacing control unit; and
showing, by the pacing control unit, one or both of surface disinfection data regarding the surface of the component or one or more visual indications for moving the assembly to disinfect various surfaces on a portion of the augmented reality sub-system as an operator moves through an environment.

Clause 28. The UV light pacing method of any of Clauses 20-27, further comprising covering the UV lamp of the assembly with one of a wire mesh screen or a stamped or laser cut metal sheet with formed apertures.

Clause 29. An ultraviolet (UV) light pacing system, comprising:

An assembly including a UV lamp configured to emit UV light to disinfect a component; and
a cover that covers the UV lamp, wherein the cover is one of a wire mesh screen or a stamped or laser cut metal sheet with formed apertures.

While various spatial and directional terms, such as top, bottom, lower, mid, lateral, horizontal, vertical, front and the like can be used to describe embodiments of the present disclosure, it is understood that such terms are merely used with respect to the orientations shown in the drawings. The orientations can be inverted, rotated, or otherwise changed, such that an upper portion is a lower portion, and vice versa, horizontal becomes vertical, and the like.

As used herein, a structure, limitation, or element that is "configured to" perform a task or operation is particularly structurally formed, constructed, or adapted in a manner corresponding to the task or operation. For purposes of clarity and the avoidance of doubt, an object that is merely capable of being modified to perform the task or operation is not "configured to" perform the task or operation as used herein.

It is to be understood that the above description is intended to be illustrative, and not restrictive. For example, the above-described embodiments (and/or aspects thereof) can be used in combination with each other. In addition, many modifications can be made to adapt a particular situation or material to the teachings of the various embodiments of the disclosure without departing from their scope. While the dimensions and types of materials described herein are intended to define the parameters of the various embodiments of the disclosure, the embodiments are by no means limiting and are exemplary embodiments. Many other embodiments will be apparent to those of skill in the art upon reviewing the above description. The scope of the various embodiments of the disclosure should, therefore, be determined with reference to the appended claims, along with the full scope of equivalents to which such claims are entitled. In the appended claims and the detailed description herein, the terms "including" and "in which" are used as the plain-English equivalents of the respective terms "comprising" and "wherein." Moreover, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

This written description uses examples to disclose the various embodiments of the disclosure, including the best mode, and also to enable any person skilled in the art to practice the various embodiments of the disclosure, including making and using any devices or systems and performing any incorporated methods. The patentable scope of the various embodiments of the disclosure is defined by the claims, and can include other examples that occur to those skilled in the art. Such other examples are intended to be within the scope of the claims if the examples have structural elements that do not differ from the literal language of the claims, or if the examples include equivalent structural elements with insubstantial differences from the literal language of the claims.

What is claimed is:

1. An ultraviolet (UV) light pacing system, comprising:
an assembly including a UV lamp configured to emit UV light to disinfect a component;

a navigation sub-system configured to track a location of the assembly within an environment; and one or more range light sources configured to emit ranging light, wherein at least one aspect of the ranging light is altered to provide a visual cue for guiding motion of the assembly to disinfect the component.

2. The UV light pacing system of claim 1, wherein the one or more range light sources are secured to the assembly.

3. The UV light pacing system of claim 1, wherein the at least one aspect comprises one or more of duration of emission of the ranging light, frequency of emission of the ranging light, color of the ranging light, or intensity of ranging light.

4. The UV light pacing system of claim 1, wherein the UV lamp is configured to emit the UV light having a wavelength between 200 nm-230 nm.

5. The UV light pacing system of claim 1, wherein the UV lamp is configured to emit the UV light having a wavelength of 222 nm.

6. The UV light pacing system of claim 1, wherein the UV lamp is configured to emit the UV light having a wavelength between 230 nm-280 nm.

7. The UV light pacing system of claim 1, wherein the UV lamp is configured to emit the UV light having a wavelength of 254 nm.

8. The UV light pacing system of claim 1, further comprising a pacing control unit in communication with the one or more range light sources, wherein the pacing control unit is configured to operate the one or more range light sources to alter the at least one aspect of the ranging light.

9. The UV light pacing system of claim 8, wherein the assembly includes the pacing control unit.

10. The UV light pacing system of claim 8, further comprising a pacing database in communication with the pacing control unit, wherein the pacing database stores surface disinfection data for one or more surfaces of one or more components.

11. The UV light pacing system of claim 10, wherein the pacing control unit shows surface disinfection information regarding the surface disinfection data for the component on a display of a user device.

12. The UV light pacing system of claim 10, wherein the pacing database further stores map data regarding at least one map of an environment, wherein the at least one map divides at least a portion of the environment into a plurality of zones, and wherein each of the plurality of zones is associated with respective surface disinfection data.

13. The UV light pacing system of claim 1, further comprising a user device including a display and a selector.

14. The UV light pacing system of claim 13, wherein the selector is configured to allow selection of a time period for at least a portion of the visual cue.

15. The UV light pacing system of claim 13, wherein the assembly comprises the user device.

16. The UV light pacing system of claim 1, further comprising a pacing control unit in communication with the assembly and the navigation sub-system, wherein the pacing control unit, based on the location of the assembly in relation to the component within the environment, automatically determines surface disinfection data for the component.

17. The UV light pacing system of claim 1, further comprising an augmented reality sub-system in communication with the assembly and a pacing control unit, wherein the pacing control unit automatically shows one or both of surface disinfection data regarding the component or one or more visual indications for moving the assembly to disinfect various surfaces on a portion of the augmented reality sub-system as an operator moves through an environment.

18. The UV light pacing system of claim 1, wherein the assembly further comprises a cover that covers the UV lamp, wherein the cover is one of a wire mesh screen or a stamped or laser cut metal sheet with formed apertures.

19. An ultraviolet (UV) light pacing method for a UV light pacing system comprising:

an assembly including a UV lamp configured to emit UV light to disinfect a component;

a navigation sub-system configured to track a location of the assembly within an environment; and one or more range light sources configured to emit ranging light, wherein at least one aspect of the ranging light is altered to provide a visual cue for guiding motion of the assembly to disinfect the component, the method comprising:

emitting the ranging light from the one or more range light sources; and altering the at least one aspect of the ranging light to provide the visual cue.

20. The UV light pacing method of claim 19, further comprising:

communicatively coupling a pacing control unit with the one or more range light sources; and operating, by the pacing control unit, the one or more range light sources to alter the at least one aspect of the ranging light.

21. The UV light pacing method of claim 20, further comprising:

communicatively coupling a pacing database in communication with the pacing control unit; and storing, within the pacing database, surface disinfection data for one or more surfaces of one or more components.

22. The UV light pacing method of claim 21, further comprising showing, by the pacing control unit, surface disinfection information regarding the surface disinfection data for the component on a display of a user device.

23. The UV light pacing method of claim 21, further comprising storing, within the pacing database, map data regarding at least one map of an environment, wherein the at least one map divides at least a portion of the environment into a plurality of zones, and wherein each of the plurality of zones is associated with respective surface disinfection data.

24. The UV light pacing method of claim 19, further comprising selecting, via a selector of a user interface a time period for at least a portion of the visual cue.

25. The UV light pacing method of claim 20, further comprising:

using the navigation sub-system to track the location of the assembly within the environment; and determining, by a pacing control unit in communication with the assembly and the navigation sub-system, surface disinfection data for the component based on the location of the assembly in relation to the component within the environment.

26. The UV light pacing method of claim 19, further comprising:

communicatively coupling an augmented reality sub-system with the assembly and a pacing control unit; and showing, by the pacing control unit, one or both of surface disinfection data regarding the component or one or more visual indications for moving the assembly to disinfect various surfaces on a portion of the augmented reality sub-system as an operator moves through an environment.

27. The UV light pacing method of claim 19, further comprising covering the UV lamp of the assembly with one of a wire mesh screen or a stamped or laser cut metal sheet with formed apertures.

28. An ultraviolet (UV) light pacing system, comprising:
an assembly including a UV lamp configured to emit UV light to disinfect a component;
one or more range light sources configured to emit ranging light, wherein at least one aspect of the ranging light is altered to provide a visual cue for guiding motion of the assembly to disinfect the component; and
an augmented reality sub-system in communication with the assembly and a pacing control unit, wherein the pacing control unit automatically shows one or both of surface disinfection data regarding the component or one or more visual indications for moving the assembly to disinfect various surfaces on a portion of the augmented reality sub-system as an operator moves through an environment.

* * * * *